(12) United States Patent
Ramsey

(10) Patent No.: US 11,890,819 B2
(45) Date of Patent: Feb. 6, 2024

(54) MULTI-CHAMBER CONTAINER FOR BIOLOGICAL MATERIALS AND COMPOUNDED PHARMACEUTICALS

(71) Applicant: Instant Systems, Inc., Norfolk, VA (US)

(72) Inventor: Tara C. Ramsey, Norfolk, VA (US)

(73) Assignee: Instant Systems, Inc., Norfolk, VA (US)

( * ) Notice: Subject to any disclaimer, the term of this patent is extended or adjusted under 35 U.S.C. 154(b) by 0 days.

(21) Appl. No.: 17/703,042

(22) Filed: Mar. 24, 2022

(65) Prior Publication Data

US 2022/0305738 A1  Sep. 29, 2022

Related U.S. Application Data

(60) Provisional application No. 63/165,696, filed on Mar. 24, 2021.

(51) Int. Cl.
| | |
|---|---|
| *B29C 65/16* | (2006.01) |
| *B29C 65/00* | (2006.01) |
| *B65D 75/20* | (2006.01) |
| *B65D 75/58* | (2006.01) |
| *B65D 75/52* | (2006.01) |
| *B29L 31/00* | (2006.01) |

(52) U.S. Cl.
CPC ........ *B29C 65/16* (2013.01); *B29C 66/53262* (2013.01); *B65D 75/20* (2013.01); *B65D 75/527* (2013.01); *B65D 75/5883* (2013.01); *B29L 2031/712* (2013.01); *B65D 2575/58* (2013.01)

(58) Field of Classification Search
CPC ... B29C 65/16; B29C 66/53262; B65D 75/20; B65D 75/527; B65D 75/5883; B65D 2575/58; B29L 2031/712
USPC ....................................................... 383/119
See application file for complete search history.

(56) References Cited

U.S. PATENT DOCUMENTS

| | | | |
|---|---|---|---|
| 1,438,487 A | 12/1922 | Greene | |
| 2,775,082 A * | 12/1956 | Vogt | B65D 75/44 53/469 |
| 2,864,492 A | 12/1958 | Lappala | |

(Continued)

FOREIGN PATENT DOCUMENTS

| | | |
|---|---|---|
| CN | 202313465 U | 7/2012 |
| EP | 1 031 341 | 11/2003 |

(Continued)

*Primary Examiner* — Peter N Helvey

(57) ABSTRACT

An apparatus for storing tissue and other biological materials includes a separable flexible container that includes a first layer coupled to a second layer via a set of seals to define a first storage volume and a second storage volume. Separate tissue specimens are containable within the first storage volume and the second storage volume. A first portion of the first layer or the second layer defines a first opening into the first storage volume. A second portion of the first layer or the second layer defines a second opening into the second storage volume. The opening into the first volume and the opening into the second volume are positioned near opposite edges of the flexible container. The separable flexible container also includes a hinge to allow the first opening and the second opening to move from location on opposing edges of the separable flexible container to adjacent locations.

22 Claims, 18 Drawing Sheets

(56) References Cited

U.S. PATENT DOCUMENTS

| | | | | |
|---|---|---|---|---|
| 2,884,988 | A * | 5/1959 | D'Angelo | B31B 70/00 156/367 |
| 3,254,828 | A * | 6/1966 | Lerner | B65B 43/267 206/820 |
| 3,326,450 | A | 6/1967 | Langdon | |
| 3,339,826 | A | 9/1967 | Beskind | |
| 3,548,723 | A * | 12/1970 | Sengewald | B31B 70/00 493/203 |
| 3,735,918 | A | 5/1973 | Tundermann | |
| 3,749,237 | A * | 7/1973 | Dorton | A61B 50/37 206/390 |
| 3,754,700 | A | 8/1973 | Bonk | |
| 4,035,304 | A | 7/1977 | Watanabe | |
| 4,152,184 | A | 5/1979 | Bacehowski | |
| 4,176,746 | A | 12/1979 | Kooi | |
| 4,181,069 | A * | 1/1980 | Porter | B31B 70/00 493/204 |
| 4,305,503 | A * | 12/1981 | Membrino | B65D 33/001 229/69 |
| 4,335,770 | A | 6/1982 | Kulle et al. | |
| 4,344,557 | A * | 8/1982 | Lerner | B65D 33/002 206/820 |
| 4,479,989 | A | 10/1984 | Mahal | |
| 4,548,023 | A | 10/1985 | Danby et al. | |
| 4,550,831 | A * | 11/1985 | Whitford | A61L 2/20 383/41 |
| 4,561,110 | A | 12/1985 | Herbert | |
| 4,581,007 | A * | 4/1986 | Kamp | B65D 33/20 493/264 |
| 4,630,448 | A | 12/1986 | Bilstad et al. | |
| 4,635,294 | A * | 1/1987 | Bentsen | B65D 33/2508 383/65 |
| 4,693,701 | A * | 9/1987 | deBin | B31B 70/00 493/227 |
| 4,699,607 | A * | 10/1987 | Lambrecht | B31B 70/643 493/204 |
| 4,714,595 | A | 12/1987 | Anthony et al. | |
| 4,863,285 | A * | 9/1989 | Claxton | B65D 31/00 383/63 |
| 4,887,715 | A * | 12/1989 | Spahn | A61B 50/37 206/370 |
| 4,925,438 | A * | 5/1990 | Wagner | B65D 33/08 493/926 |
| 4,945,713 | A * | 8/1990 | Widenback | B65B 43/123 53/469 |
| 4,998,671 | A | 3/1991 | Leifheit | |
| 5,007,744 | A * | 4/1991 | Scarberry | B65D 75/46 493/194 |
| 5,031,762 | A | 7/1991 | Heacox | |
| 5,088,994 | A | 2/1992 | Porat et al. | |
| 5,114,004 | A | 5/1992 | Isono et al. | |
| 5,118,202 | A * | 6/1992 | Bruno | B65D 75/5805 383/203 |
| 5,160,329 | A | 11/1992 | Oxley | |
| 5,209,745 | A | 5/1993 | Irr et al. | |
| 5,221,567 | A * | 6/1993 | Baker | B31B 70/00 493/194 |
| D337,382 | S | 7/1993 | Wallace | |
| 5,226,858 | A * | 7/1993 | Snowdon | B65D 33/001 493/204 |
| 5,236,088 | A | 8/1993 | Dhority et al. | |
| 5,253,754 | A | 10/1993 | Soodak | |
| 5,266,140 | A * | 11/1993 | Kohno | B42C 7/002 156/244.14 |
| 5,309,698 | A * | 5/1994 | Huseman | B65D 33/2508 53/459 |
| 5,360,413 | A | 11/1994 | Leason et al. | |
| 5,370,221 | A | 12/1994 | Magnusson | |
| 5,728,086 | A | 3/1998 | Niedospial | |
| 5,804,265 | A | 9/1998 | Saad et al. | |
| RE36,132 | E | 3/1999 | Heacox | |
| 5,971,155 | A * | 10/1999 | Liang | B65D 33/2508 383/65 |
| 6,022,344 | A | 2/2000 | Meijer et al. | |
| 6,045,546 | A | 4/2000 | Drago et al. | |
| 6,089,541 | A | 7/2000 | Weinheimer et al. | |
| 6,149,302 | A | 11/2000 | Taheri | |
| 6,176,371 | B1 | 1/2001 | Tyrrell | |
| 6,287,284 | B1 | 9/2001 | Warburton-Pitt | |
| 6,367,634 | B1 | 4/2002 | Lynn et al. | |
| 6,394,993 | B1 * | 5/2002 | Chang | A61J 1/10 383/202 |
| 6,398,771 | B1 | 6/2002 | Gustafsson et al. | |
| 6,419,392 | B1 * | 7/2002 | Baker | B31B 70/00 206/439 |
| 6,422,753 | B1 * | 7/2002 | Thomas | B65D 75/5811 383/906 |
| 6,523,698 | B1 | 2/2003 | Dennehey et al. | |
| 6,579,008 | B2 * | 6/2003 | Price | B65D 33/2541 383/38 |
| 6,648,133 | B1 | 11/2003 | Blaschke et al. | |
| 6,730,071 | B1 | 5/2004 | Dassa | |
| 6,773,425 | B1 | 8/2004 | Tamari | |
| 6,945,695 | B2 * | 9/2005 | Rabiea | B65B 43/267 383/35 |
| 7,051,879 | B2 | 5/2006 | Ramet | |
| 7,121,064 | B2 * | 10/2006 | Ausnit | B65B 9/093 53/139.2 |
| 7,354,426 | B2 | 4/2008 | Young | |
| D595,842 | S | 7/2009 | Haga et al. | |
| 7,594,578 | B2 | 9/2009 | Smith et al. | |
| 7,670,384 | B2 | 3/2010 | Kumar et al. | |
| 7,674,039 | B2 | 3/2010 | McMahon et al. | |
| 7,770,611 | B2 | 8/2010 | Houwaert et al. | |
| 7,810,667 | B2 * | 10/2010 | Douglas | G07F 11/68 206/390 |
| 7,875,015 | B2 | 1/2011 | Pahlberg et al. | |
| 8,038,348 | B2 * | 10/2011 | Lerner | B29C 66/83433 383/3 |
| 8,136,330 | B2 | 3/2012 | Ostler et al. | |
| 8,267,912 | B2 | 9/2012 | Ferris | |
| 8,287,680 | B2 | 10/2012 | Foucaut et al. | |
| 8,591,391 | B2 | 11/2013 | Chavarria et al. | |
| 8,597,223 | B2 | 12/2013 | D'Ayot et al. | |
| D705,443 | S | 5/2014 | Ichimura et al. | |
| 9,095,499 | B2 | 8/2015 | Kugelmann et al. | |
| 9,155,606 | B2 | 10/2015 | Benoit et al. | |
| 9,198,830 | B2 | 12/2015 | Kugelmann et al. | |
| 9,796,166 | B2 | 10/2017 | Verri et al. | |
| 9,879,217 | B2 | 1/2018 | Coupier | |
| 9,926,524 | B2 | 3/2018 | Clark et al. | |
| 9,962,898 | B1 * | 5/2018 | Russell | B65D 75/008 |
| 9,974,528 | B2 | 5/2018 | Taylor et al. | |
| 10,111,739 | B2 | 10/2018 | Benoit et al. | |
| 10,582,994 | B2 | 3/2020 | Kapec et al. | |
| 11,058,530 | B2 | 7/2021 | Chen et al. | |
| 11,065,095 | B2 | 7/2021 | Alden et al. | |
| 11,155,374 | B2 | 10/2021 | Thesing et al. | |
| 11,332,282 | B2 | 5/2022 | Murray | |
| 2002/0130093 | A1 | 9/2002 | Ferrara, Jr. et al. | |
| 2003/0009989 | A1 | 1/2003 | Knoerzer et al. | |
| 2003/0075474 | A1 | 4/2003 | Moyer et al. | |
| 2003/0089084 | A1 * | 5/2003 | Ausnit | B65B 61/188 53/133.4 |
| 2004/0134166 | A1 * | 7/2004 | Ausnit | B65B 9/093 53/412 |
| 2004/0161167 | A1 | 8/2004 | Ausnit et al. | |
| 2005/0261659 | A1 * | 11/2005 | Mizuo | B29C 65/02 604/410 |
| 2005/0271307 | A1 | 12/2005 | Pawloski et al. | |
| 2006/0024818 | A1 | 2/2006 | Conconi | |
| 2007/0074980 | A1 | 4/2007 | Bankoski et al. | |
| 2007/0092398 | A1 | 4/2007 | McDonald | |
| 2007/0206888 | A1 | 9/2007 | Chang | |
| 2008/0017543 | A1 | 1/2008 | Pahlberg et al. | |
| 2008/0214998 | A1 | 9/2008 | Kurek et al. | |
| 2008/0234654 | A1 | 9/2008 | McCarthy et al. | |
| 2008/0254471 | A1 | 10/2008 | Bordano | |
| 2008/0285896 | A1 | 11/2008 | Taheri | |
| 2008/0304771 | A1 * | 12/2008 | Harder | B65D 33/25 383/203 |

(56) References Cited

U.S. PATENT DOCUMENTS

| | | |
|---|---|---|
| 2009/0030396 A1 | 1/2009 | Ferris |
| 2009/0034885 A1* | 2/2009 | McGruder ............. B65D 33/25 383/38 |
| 2009/0105684 A1 | 4/2009 | Balteau et al. |
| 2009/0238495 A1 | 9/2009 | Anderson |
| 2010/0040308 A1* | 2/2010 | McLellan ............ B65D 33/004 383/103 |
| 2011/0308977 A1 | 12/2011 | DiLiberto et al. |
| 2011/0308992 A1 | 12/2011 | Bahcall |
| 2012/0195533 A1 | 8/2012 | Mead |
| 2013/0209000 A1 | 8/2013 | Owensby et al. |
| 2013/0281964 A1 | 10/2013 | Kugelmann et al. |
| 2015/0216763 A1 | 8/2015 | Fearnot |
| 2016/0000062 A1 | 1/2016 | Chen et al. |
| 2016/0052690 A1 | 2/2016 | Bolhous et al. |
| 2016/0137354 A1* | 5/2016 | Sargin ................. B65D 33/002 383/10 |
| 2016/0177245 A1 | 6/2016 | Johnson et al. |
| 2016/0228231 A1 | 8/2016 | Southard et al. |
| 2016/0305577 A1 | 10/2016 | Huschke |
| 2017/0001782 A1 | 1/2017 | Arent et al. |
| 2017/0121061 A1 | 5/2017 | Sprehe et al. |
| 2017/0172847 A1 | 6/2017 | Platenkamp et al. |
| 2017/0181426 A1 | 6/2017 | Wolf et al. |
| 2017/0202740 A1 | 7/2017 | Yoshida et al. |
| 2018/0154289 A1 | 6/2018 | Rhodes |
| 2018/0249703 A1 | 9/2018 | Ilyin |
| 2020/0008921 A1 | 1/2020 | Alden et al. |
| 2020/0061365 A1 | 2/2020 | Alden et al. |
| 2021/0269213 A1 | 9/2021 | Burley et al. |
| 2021/0298888 A1 | 9/2021 | Alden et al. |
| 2022/0273464 A1 | 9/2022 | Rister et al. |
| 2023/0233309 A1 | 7/2023 | Alden et al. |

FOREIGN PATENT DOCUMENTS

| | | |
|---|---|---|
| WO | WO1997/042897 | 11/1997 |
| WO | WO2002/041824 | 5/2002 |
| WO | WO2017/026131 | 2/2017 |
| WO | WO 2020/014162 | 1/2020 |
| WO | WO 2022/261389 | 12/2022 |

* cited by examiner

MULTI-CHAMBER CONTAINER FOR BIOLOGICAL MATERIALS AND COMPOUNDED PHARMACEUTICALS

CROSS-REFERENCE TO RELATED APPLICATIONS

This application is a non-provisional application that claims priority to U.S. Provisional Application Ser. No. 63/165,696, entitled "Multi-Chamber Container for Biological Materials and Compounded Pharmaceuticals," filed Mar. 24, 2021, which is incorporated herein by reference in its entirety.

BACKGROUND

The embodiments described herein relate to containers for storing, packaging and transporting tissue and other biological material. More particularly, one or more of the embodiments described herein relate to devices and methods including containers having separate but interconnected storage volumes.

Known tissue implants and/or grafts are used in a variety of procedures to repair or replace damaged tissue. Such procedures can include implanting bone or gum tissue to address dental or periodontal issues, bone grafting to repair fractures, and tendon grafting to repair damaged ligaments and/or tendons (e.g., repair of a torn anterior cruciate ligament), to name just a few. In many instances, the tissue implant is not taken from the patient's body (i.e., is not an autograft), but rather is from another source, such as from a human cadaver (i.e., an allograft) or an animal (i.e., a xenograft). Known non-autologous grafts are often stored in a dried condition within a sterile package, and thus must be rehydrated or otherwise prepared prior to use.

Some known procedures for preparing or rehydrating a tissue implant include removing the tissue implant from the sterile package and placing the tissue graft in an opened container (e.g., a basin) that contains rehydration liquid. The tissue implant is then manipulated within the open container to facilitate rehydration. Such manipulation can include, for example, manually submerging the tissue implant within the rehydration fluid (in an effort to achieve consistent rehydration), agitating the tissue implant and/or rehydration fluid, and the like. After rehydration, the tissue implant is then removed from the rehydration container for use. This procedure can result in compromised sterility (e.g., due to the repeated transfer of the tissue graft), inconsistent rehydration due to inconsistent exposure of the tissue implant in the open container, and longer rehydration times. Moreover, the packaging in the related art include only a single chamber container for storing tissue and/or biological material. Thus when less than an entire portion of the tissue and/or biological material is needed for a particular procedure, the remaining portion is wasted and discarded since sterility is compromised after the opening of the single chamber container. Additionally, because of the repeated movement of the tissue implant (e.g., during transfer and while in the rehydration container) possible damage to the tissue implant can occur.

Other known procedures include receiving the tissue implant in a rigid tray, removing a lid from the tray, and completing the rehydration procedure in the open tray. Although this method eliminates the step of transferring the tissue implant from its sterile packaging, such rigid packaging can be bulky and less desirable for tissue storage facilities. Moreover, the rehydration still occurs in an open top container and can involve agitating, submerging, or moving the tissue implant, which can result in damage to the tissue implant.

Yet other known procedures including rehydrating the tissue implant within a single product or volume sterile flexible pouch. Such systems and methods often provide inadequate resources and flexibility of resource options during procedure slowing down the procedures and causing waste. The loading of single packages and storing multiple single packages of biological material is also cumbersome wasting time and space.

Yet other known procedures including freezing the tissue implant within a single product or volume sterile flexible pouch. Such systems and methods often provide inadequate resources and flexibility of resource options during procedure slowing down the procedure and causing waste or causing the opening of a second single packaged product, also slowing down the procedure and causing waste.

Yet other known procedures including room temperature storage within a single product or volume sterile flexible pouch. Such systems and methods often provide inadequate resources and flexibility of resource options during procedure slowing down the procedure and causing waste or causing the opening of a second single packaged product, also slowing down the procedure and causing waste.

Thus, a need exists for improved containers and methods for storing, transporting, processing, and/or rehydrating multiple units of tissue and/or other biological material.

SUMMARY

Containers and methods for storing tissue and other biological materials are described herein. In some embodiments, an apparatus includes a separable flexible container. The separable flexible container includes a first layer coupled to a second layer via a plurality of seals to define at least a first storage volume and a second storage volume. Separate tissue specimens are suitably containable within the respective first storage volume and the second storage volume for use in one or more medical procedures. A first portion of the first layer or the second layer defines a first opening into the first storage volume. A second portion of the first layer or the second layer defines a second opening into the second storage volume. The opening into the first volume and the opening into the second volume are positioned near opposite edges of the flexible container. The separable flexible container also includes a hinge suitable to allow the first opening and the second opening to move from opposing location on opposing edges of the separable flexible container to adjacent locations. The separable flexible container includes a first frangible region positioned along the seals and configured for separation of the storage volumes. The separable flexible container a second frangible region configured for opening the container after sealing the tissue specimen therein by forming a separation between the first layer and the second layer or an opening through at least one of the first layer or the second layer.

In some embodiments, a method includes inserting a first tissue specimen into a first storage volume defined between a first layer of a flexible container and a second layer of the flexible container. The tissue specimen is inserted via an opening defined by an edge of the first layer and an edge of the second layer. Inserting a second tissue specimen via a second opening. The second tissue specimen is positioned within the second storage volume between the first layer and a support structure. The edge of the first layer is then coupled to the edge of the second layer to form a peelable seal that hermetically seals the storage volume. The peelable seal is configured such that the first layer can be peeled away from the second layer to expose at least one of the storage volumes. Each of the storage volumes are separated from one another by tearing along frangible regions.

DETAILED DESCRIPTION

Figure 1:
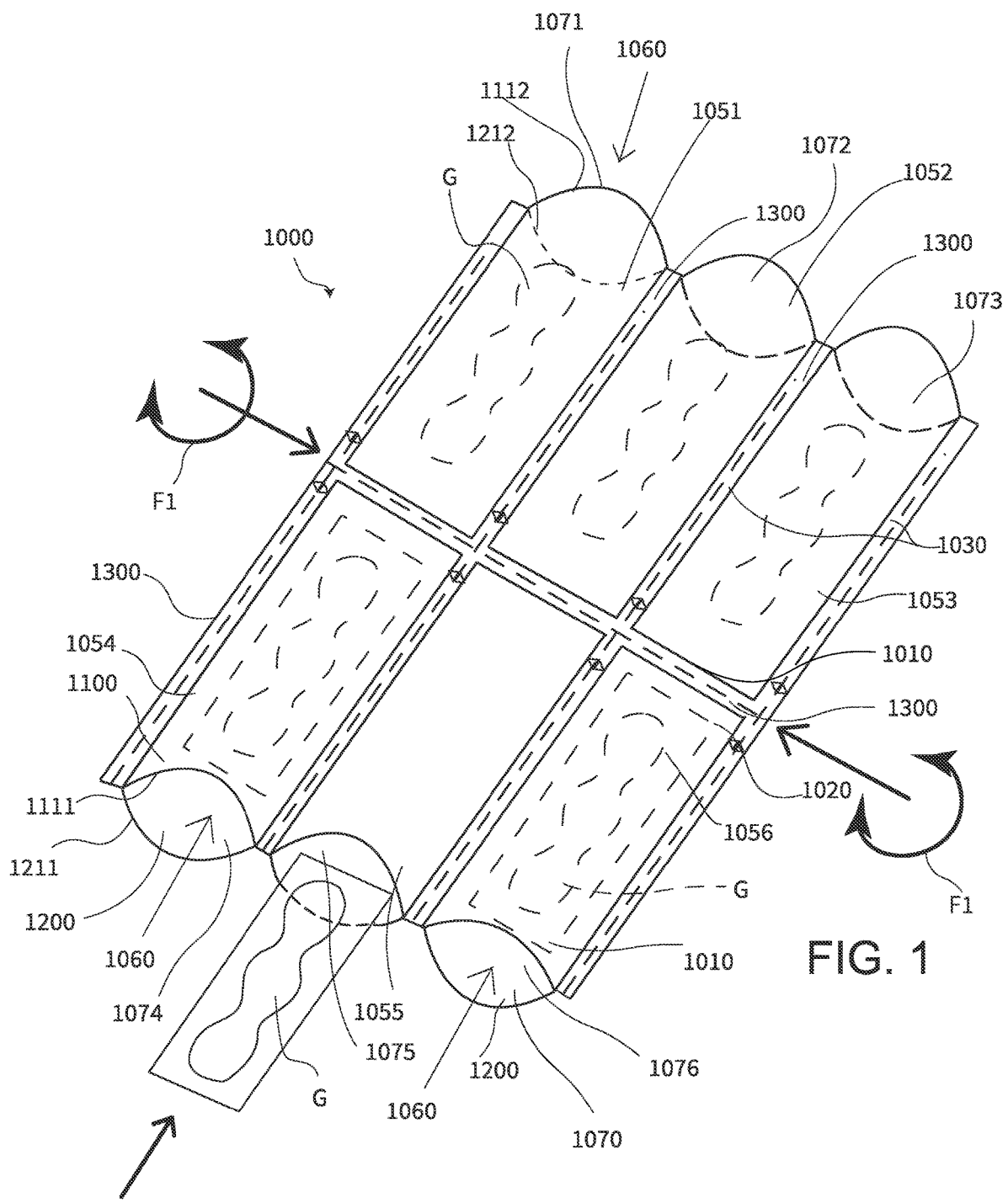
FIG. 1 is a schematic illustration of a multi-chamber container assembly, in a first configuration, according to an embodiment.

The embodiments described herein can advantageously be used in a wide variety of tissue and/or biologic materials for storage, transportation, processing and/or implantation operations. In particular, the separable container assemblies described herein can allow for a tissue specimen and/or biologic material to be loaded and sealed at the point of loading (e.g., a tissue bank) via connected, but separate, multi-chamber volumes (each volume being individually separable from the separable container assembly). The loaded multi-chamber volumes of the separable container assembly can be used to both store and protect multiple units of the tissue specimen and/or biologic materials (e.g., microaliquots) within the same container assembly. Moreover, although the container is flexible and easily adaptable for storage, the separable container assemblies described herein include multiple internal storage volumes suitable for retaining multiple different tissue specimens or biologic materials together in a single container assembly or multiple biologic materials with non-biologic materials, but in their respective storage volumes. Additionally, or alternatively, the same stored product can be sub-divided into small units and stored together in a single container assembly, but in their respective storage volumes. In some embodiments, the stored product can be packaged together sequentially or in parallel to improve loading efficiency into the container assembly and to minimize waste. In some embodiments, the stored product can be transported together and stored together. In some embodiments, one or more of the multi-chamber volumes can be separated from the container assembly such that a user (e.g., surgeon) can select an appropriate unit or units of stored product to be used for a particular procedure while maintaining the sterility of the units not used and retained within the container assembly. In this manner, the separable container assemblies described herein can result in more efficient loading of tissue and/or biological samples, enable the same identical or related tissue and/or biological samples to be stored together in a single container assembly, and enable a user to select an appropriate amount of tissue and/or biological materials to use for a single procedure without adversely affecting the sterility of the tissue and/or biological materials remaining with the separable container assembly.

In some embodiments, multiple stored product can be stored within respective storage volumes of the container assembly, transported together as part of the same container assembly, and frozen together as part of the same container assembly (e.g., cryogenically frozen down to about −200° C.). In some embodiments, the entire container assembly is thawed. In some embodiments, one or more of the separable flexible containers of the container assembly can be removed from the container assembly and thawed individually. In some embodiments, unused separable flexible containers of the container assembly can be re-frozen. In some embodiments the container assembly can be inserted into an overwrap or into one separable flexible containers of a multi-chamber overwrap assembly.

In some embodiments, a method of rehydrating a tissue specimen includes conveying a rehydration fluid into a storage volume defined between a first layer of a flexible container and a second layer of the flexible container. The rehydration fluid is conveyed via a port coupled to the flexible container. The storage volume contains a tissue specimen hermetically sealed therein, and the tissue specimen is supported by a support structure. A stiffness of the support structure is greater than each of a stiffness of the first layer and a stiffness of the second layer. The rehydration fluid is maintained within the storage volume to rehydrate the tissue specimen. The first layer is then peeled from the second layer to expose the storage volume. The method further includes removing the rehydrated tissue specimen from the storage volume after the first layer is peeled.

As used herein, the term "about" when used in connection with a referenced numeric indication means the referenced numeric indication plus or minus up to 10% of that referenced numeric indication. For example, the language "about 50" covers the range of 45 to 55. Similarly, the language "about 5" covers the range of 4.5 to 5.5.

As used herein, the term tissue specimen or tissue graft refers to any material that can be used in a tissue repair procedure. Thus, a tissue specimen or a tissue graft can include any of a skin graft, bone tissue, fiber tissue (e.g., tendon tissue, ligament tissue, or the like), ocular tissue (e.g. corneal implants), cardiovascular tissue (e.g., valves, veins, arteries, or the like) or cellular products (stem cells, blood cells, or the like) or the like. A tissue specimen or a tissue graft can include a portion of tissue harvested from a donor or a structure component that includes both tissue and non-tissue material (e.g., a synthetic matrix that includes tissue therein). For example, a tissue specimen or a tissue graft can include bone tissue that also includes bone cement or other non-tissue components. As another example, a tissue specimen or tissue graft can include bone chips including cortical bone chips, cancellous bone chips, and corticocancellous bone chips, and/or bone chips with viable bone lineage committed cells. As another example, a tissue specimen, tissue graft, or biological material can include birth tissue including placenta, amnion, chorion, umbilical, or the like.

As used herein, the term "stiffness" relates to an object's resistance to deflection, deformation, and/or displacement produced by an applied force, and is generally understood to be the opposite of the object's "flexibility." For example, a layer or structure of a container with greater stiffness is more resistant to deflection, deformation and/or displacement when exposed to a force than is a layer or structure of the container having a lower stiffness. Similarly stated, a container (or layer) having a higher stiffness can be characterized as being more rigid than a container (or layer) having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance maybe measured as the deflection of the portion of the object different than the portion of the object to which the force is directly applied. Said another way, in some objects, the point of deflection is distinct from the point where the force is applied.

Stiffness (and therefore, flexibility) is an extensive property of the object being described, and thus is dependent upon the material from which the object is formed as well as certain physical characteristics of the object (e.g., cross-sectional shape, thickness, boundary conditions, etc.). For example, the stiffness of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be decreased, for example, by introducing into the object and/or constructing the object of a material having a relatively low modulus of elasticity. Similarly, the flexural modulus is used to describe the ratio of an applied stress on an object in flexure to the corresponding strain in the outermost portions of the object. The flexural modulus, rather than the modulus of elasticity, is often used to characterize certain materials, for example plastics, that do not have material properties that are substantially linear over a range of conditions. An object with a first flexural modulus is more elastic and has a lower strain on the outermost portions of the object than an object with a second flexural modulus greater than the first flexural modulus. Thus, the stiffness of an object can be reduced by including in the object a material having a relatively low flexural modulus.

Moreover, the stiffness (and therefore flexibility) of an object constructed from a polymer can be influenced, for example, by the chemical constituents and/or arrangement of the monomers within the polymer. For example, the stiffness of an object can be reduced by decreasing a chain length and/or the number of branches within the polymer. The stiffness of an object can also be reduced by including plasticizers within the polymer, which produces gaps between the polymer chains.

The stiffness of an object can also be increased or decreased by changing a physical characteristic of the object, such as the shape or cross-sectional area of the object. For example, an object having a length and a cross-sectional area may have a greater stiffness than an object having an identical length but a smaller cross-sectional area. As another example, the stiffness of an object can be reduced by including one or more stress concentration risers (or discontinuous boundaries) that cause deformation to occur under a lower stress and/or at a particular location of the object. Thus, the stiffness of the object can be decreased by decreasing and/or changing the shape of the object.

As used in this specification, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes include various spatial device positions and orientations.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

FIGS. 1-5 are schematic illustrations of a multi-chamber container assembly 1000 (also referred to herein as container assembly) according to an embodiment. The container assembly 1000 (or any other package, pouch, bag, or container assemblies described herein) includes internal containers configured to suitably store one or more of a tissue, cellular material, biological material (including but not limited to biological material G, as described herein), and/or related media (herein referred to together as stored product). In some embodiments, the container assemblies described herein can be used to store packages containing tissue, cellular material, biological material or related media. In some embodiments, the stored product can include biologic materials, including but not limited to, human and animal tissues, human and animal cells or cellular materials, plant materials (tissue and cellular materials), organs, organoids, biologically sourced materials (e.g., printed tissues, cells, organs, or organoids), bacteria, viruses, viral vectors, fungi, medical devices, combination devices, material for homologous or non-homologous use, and/or materials for autologous or allogenic use. In some embodiments, the stored product can include cellular material, including but is not limited to, lineage committed and non-lineage committed cells (e.g. bone lineage committed cells, osteoblasts, osteocytes, etc.), differentiated cells or non-differentiated cells (e.g., muscle cells, endothelial cells, etc.), and/or genetically modified or non-genetically modified materials. Examples of human and animal tissues include, but is not limited to, birth tissues (e.g., amnion, cord, cord blood, chorion, placenta, etc.), bones and/or products made from bones (e.g., machined allografts, ground particles, etc.), bone sources (e.g., tibia, fibula, humerus, cranial flaps, radius, ulna, pelvic bones, and joints, etc.), brain tissue, cartilages (from all sources in bodies generally from knee joints, shoulders, etc.), fascia lata, heart valves, arteries, veins, nerves, organs (e.g., lungs, hearts, liver, kidneys, etc.), reproduction tissue (e.g., semen and eggs), ribs, soft tissues (e.g., all tendons, Achilles, patellar, etc.), skin, and/or tumors. Examples of the human or animal cellular materials include, but is not limited to, B-cells, blood cells and blood derived cells, bone cells, CAR-T cells, egg cells, engineered T-Cells, fat cells, muscle, cells, natural killer cells, nerve cells, sperm cells, stem cells (modified and un-modified, differentiated and non-differentiated), T-cells, tumor infiltrating lymphocytes (TIL), viral vectors, viruses and bacteria. The human or animal cellular material can be modified or non-modified (such as genetically modified). Examples of the plant materials include, but is not limited to, cellulose, hemicellulose, pectin, fruit, fungi, leaves, mitochondria, plant organelles, pollen, roots, seeds, shoots, and/or stems. In some embodiments, the stored product can include related media, including but not limited to, culture media, saline solution, cryoprotectant, preservation solution, etc. It will be appreciated that any suitable stored product can be stored within any of the container assemblies described herein.

Figure 4:
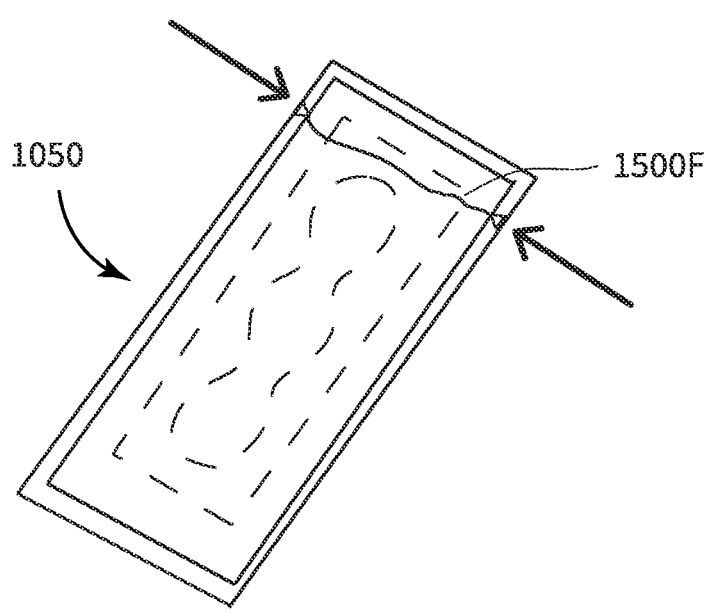
FIG. 4 is a schematic illustration of the multi-chamber container assembly of FIG. 1, in a fourth configuration.
Figure 5:
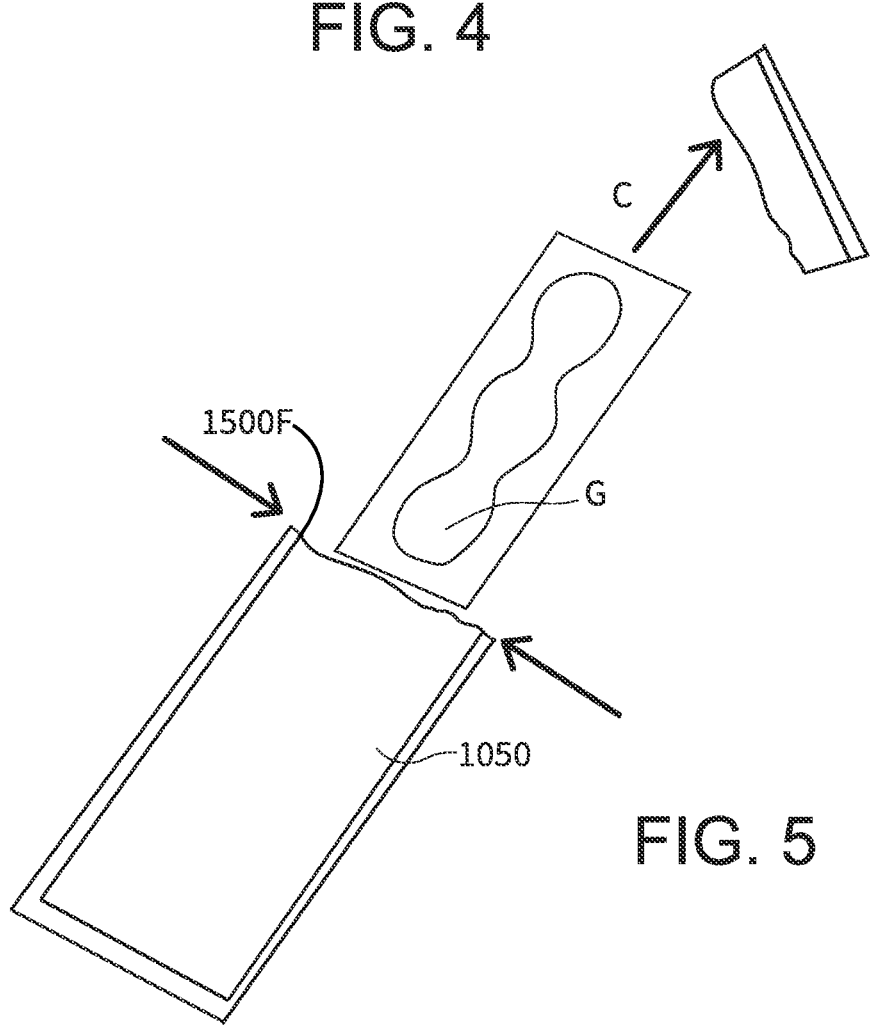
FIG. 5 is a schematic illustration of the multi-chamber container assembly of FIG. 1, in a fifth configuration.

The container assembly 1000 is shown in a first (or open partially) configuration (FIG. 1), a second (or sealed) configuration (FIG. 2), a third (or separating) configuration (FIG. 3), a fourth (or separated) configuration (FIG. 4) and, a fifth (or open) configuration with the contents removed (FIG. 5). The container assembly 1000 (and any of the container assemblies described herein) can be used to store any of the tissue and biological materials described herein, and/or to perform any of the methods described herein, such as the method 10 of preparing a tissue specimen for storage (see FIG. 11) and/or the methods of rehydrating a tissue specimen for use in a procedure. As described herein, the container assembly 1000 provides a container that can be used for storage, transport, processing, and/or rehydration of a tissue specimen and/or biologic materials. The container assembly 1000 also includes a first layer 1100, a second layer 1200 and one or more seals 1300 connecting the first layer 1100 and the second layer 1200. The one or more seals 1300 form side edges and a center seam of separable, multiple separable flexible containers 1050, 1051, 1052, 1053, 1054, 1055, and 1056.

Each of the multiple separable flexible containers 1050, 1051, 1052, 1053, 1054, 1055, 1056 includes a first end portion 1010, a second end portion 1020, and a pair of side edges 1030 between the first end portion 1010 and the second end portion 1020. The separable flexible container 1050, 1051, 1052, 1053, 1054, 1055, 1056 is constructed from a first layer 1100 and a second layer 1200 coupled together to define a storage volume 1060. As shown in FIG. 1, when the container assembly 1000 is in the first (or opened) configuration, one or more edges (e.g., edges 1111 and/or 1112) of the first layer 1100 is spaced apart from one or more edges (e.g., edges 1211 and/or 1212) of the second layer 1200 to define a plurality of openings 1070, 1071, 1072, 1073, 1074, 1075, 1076 into the storage volume 1060 of each of the separable flexible containers 1050, 1051, 1052, 1053, 1054, 1055, 1056. The opening 1070, 1071, 1072, 1073, 1074, 1075, 1076 can be of any suitable size to facilitate loading of the tissue, biological material and/or treatment G (e.g., a tissue graft), as described herein. In some embodiments, a support structure 1600 is used to support the material G. The opening 1070, 1071, 1072, 1073, 1074, 1075, 1076 can be a suitable size to facilitate the loading of the support structure 1600. As shown in FIGS. 1-5, some materials G are supported and some are not. In some embodiments, the opening 1070 can extend across a portion of the length of an end or a side of the separable flexible container 1050, 1051, 1052, 1053, 1054, 1055, 1056. In some embodiments, the opening 1070, 1071, 1072, 1073, 1074, 1075, 1076 can extend across substantially all of the end or side of the separable flexible container 1050, 1051, 1052, 1053, 1054, 1055, 1056. As shown in FIGS. 1-5, the container assembly 1000 can include multiple openings along multiple edges (e.g., opposing edges 1111, 1211 and 1211, 1212 as shown).

Figure 16:
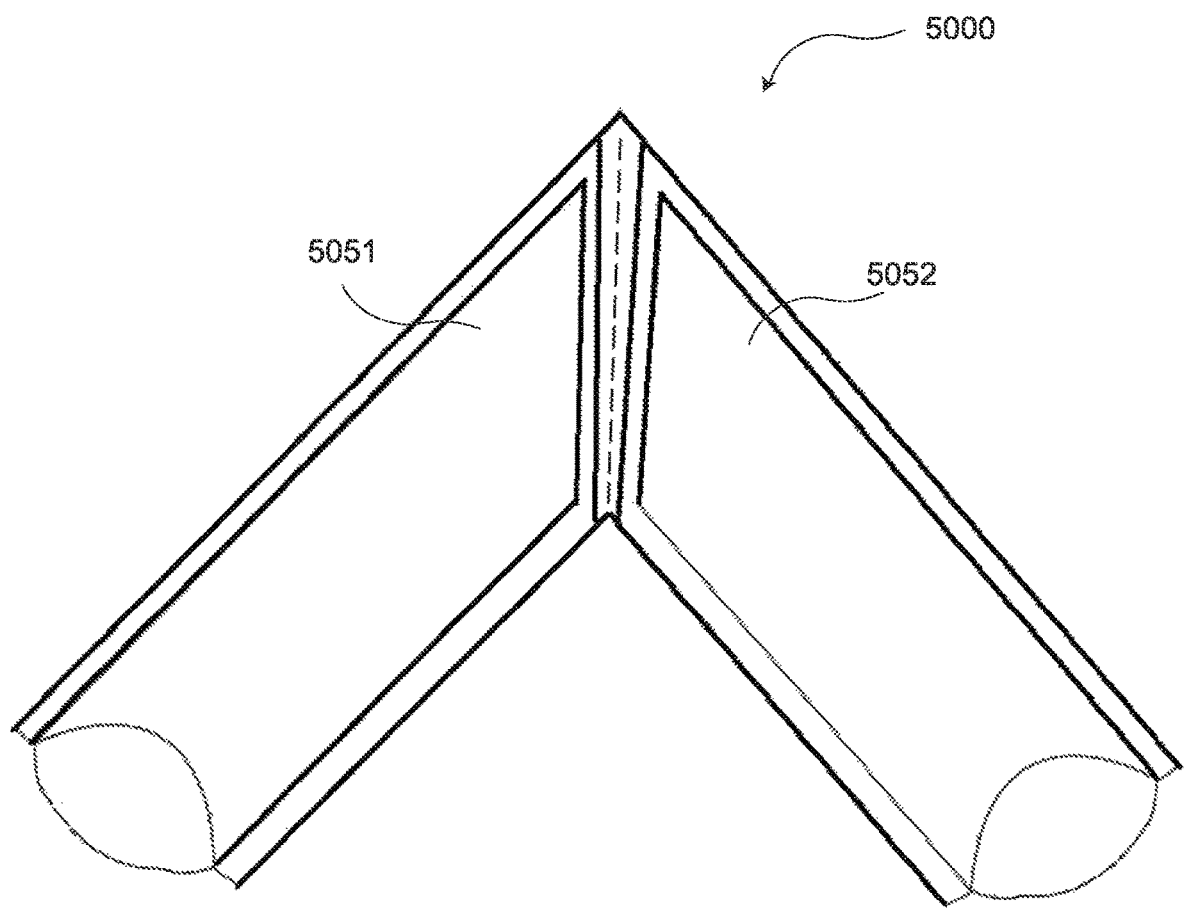
FIG. 16 is a schematic illustration of a multi-chamber container assembly according to an embodiment.
Figure 17:
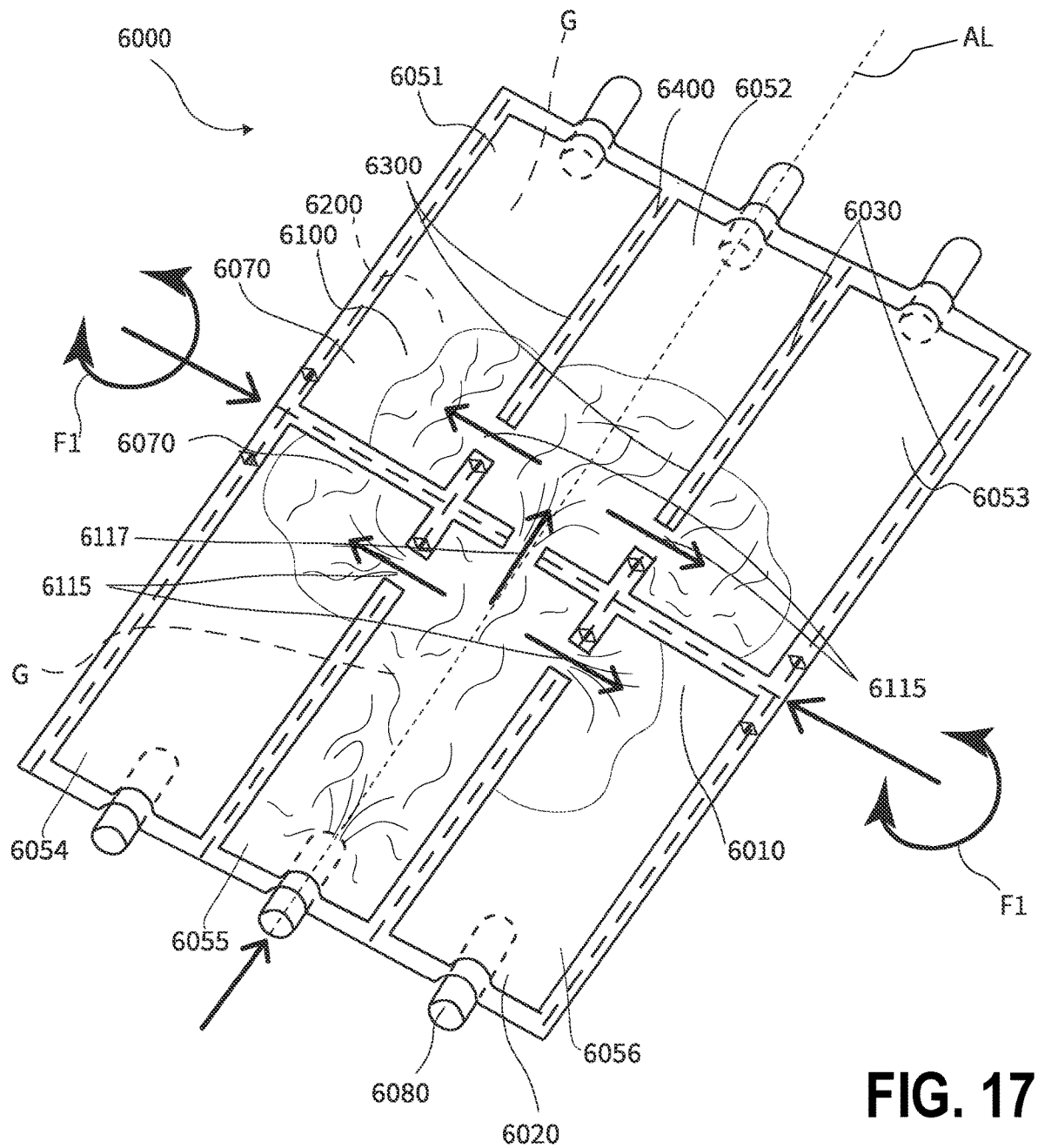
FIG. 17 is a schematic illustrations of a multi-chamber container assembly, in a first configuration, according to an embodiment.

Although six separable flexible containers 1051, 1052, 1053, 1054, 1055, 1056 are shown for the container assembly 1000, it will be appreciated that a container assembly can include two or more flexible containers. For example, as shown in FIG. 16, a container assembly 4000 includes a first separable flexible container 4051 and a second separable flexible container 4052. By way of another example, the overwrap assembly 3000 (which will be described in greater detail below) includes a first separable flexible container 3051, a second separable flexible container 3052, and a third separable flexible container 3053. By way of yet another example, as shown in FIG. 17, a container assembly 5000 includes a separable flexible container 5051 and a second separable flexible container 5052. Each of the separable flexible containers 5051, 5052 include a tapered end joined to one another. The container assembly 5000 defines a generally V-shaped perimeter and may be suitable for insertion into an overwrap assembly, such as the overwrap assembly 3000 described in greater detail below.

In some embodiments, a container assembly can include 2 to 100 separable flexible containers. However, it will be appreciated that any number of separable flexible containers can be included in a single container assembly depending on the desired application. In some embodiments, a container assembly can include multiple rows of separable flexible containers. For example, as shown in FIG. 1, the container assembly 1000 includes two rows of three separable flexible containers. The first row includes separable flexible containers 1051, 1052, 1053. The second row includes separable flexible containers 1054, 1055, 1056. In some embodiments, a container assembly can include 2 to 10 rows of multiple, separable flexible containers. The single flexible container also can include one or more of the features, characteristics and/or components discussed with regards to any one or more of the multiple separable flexible containers 1050, 1051, 1052, 1053, 1054, 1055, 1056 as applicable to a single flexible container.

The first and second layers 1100, 1200 respectively can be constructed of any suitable material. The first layer 1100 can have a first stiffness and the second layer 1200 can have a second stiffness. In some embodiments, the stiffnesses of the first layer 1100 and the second layer 1200 are the same. In some embodiments the stiffnesses are different. In some embodiments the second stiffness is greater than the first stiffness. In some embodiments, the first stiffness is greater than the second stiffness. In some embodiments, the layers 1100, 1200 respectively can be constructed from the same material. In some embodiments, the layers 1100, 1200 respectively can be constructed from a different material and the second stiffness can be different than the first stiffness. In some embodiments, the first layer 1100 can be a thin, peelable film. The first layer 1100 can have any suitable thickness to provide the desired strength, flexibility, and sealing characteristics. For example, in some embodiments, the first layer 1100 can be between about 10 microns (0.010 mm) and about 2000 microns (2.0 mm). In some embodiments, the first layer 1100 can be between about 50 microns (0.050 mm) and about 200 microns (0.200 mm). In some embodiments, the first layer can be between about 50 microns (0.050 mm) and about 1000 microns (0.100 mm). The second layer 1200 can have any suitable thickness to provide the desired strength, flexibility, and sealing characteristics. For example, in some embodiments, the first layer 1200 can be between about 10 microns (0.010 mm) and about 2000 microns (2.0 mm). In some embodiments, the second layer 1200 can be between about 50 microns (0.050 mm) and about 200 microns (0.200 mm). In other embodiments, the second layer 1200 can be between about 50 microns (0.050 mm) and about 1000 microns (0.100 mm).

In some embodiments, the layers 1100, 1200 of the container assembly 1000 (or the material of any of the container assemblies described herein) can be produced out of any one or more of the following materials: polyethylene (PE), low density polyethylene (LDPE), composites of LDPE, linear low-density polyethylene (LLDPE), high density poly ethylene (HDPE), polychlorotrifluoroethylene (PCTFE), ethylene tetrafluoroethylene (ETFE), polytetrafluoroethylene (PTFE), fluorinated ethylene propylene (FEP), polyurethane, polyimides (coats or non-coated), polyvinyl chloride (PVC), perfluoroalkoxy alkane (PFA), ethylene-vinyl acetate (EVA), polyvinylidene fluoride or polyvinylidene difluoride (PVDF), THV (a polymer of tetrafluoroethylene, hexafluoropropylene and vinylidene fluoride), PFE (Poly(fluorenylene ethynylene)), nylon, and/or composite of nylon. In some embodiments, any of the multi-chamber packaging using the materials above can be co-extruded and/or laminated. In some embodiments, any of the multi-chamber packaging using the materials above can further include aluminum foil laminate, aluminum oxide laminate, or laminated or co-extruded with aluminum oxide. In some embodiments, any of the multi-chamber packaging can be laminated with a layer of alder or any other suitable adhesive. In some embodiments, any of the multi-chamber container assemblies (e.g., 1000, 2000, 3000) described herein can be produced using a plasma treatment, and/or a corona treatment. In some embodiments, the material of the first layer 1100 and the material second layer 1200 are the same. In other embodiments, the material of the first layer 1100 is different from the material of the second layer 1200. For example, the material and/or thickness of the second layer 1200 may be selected such that a rigidity of the second layer 1200 is greater than the rigidity of the first layer 1100.

Figure 2:
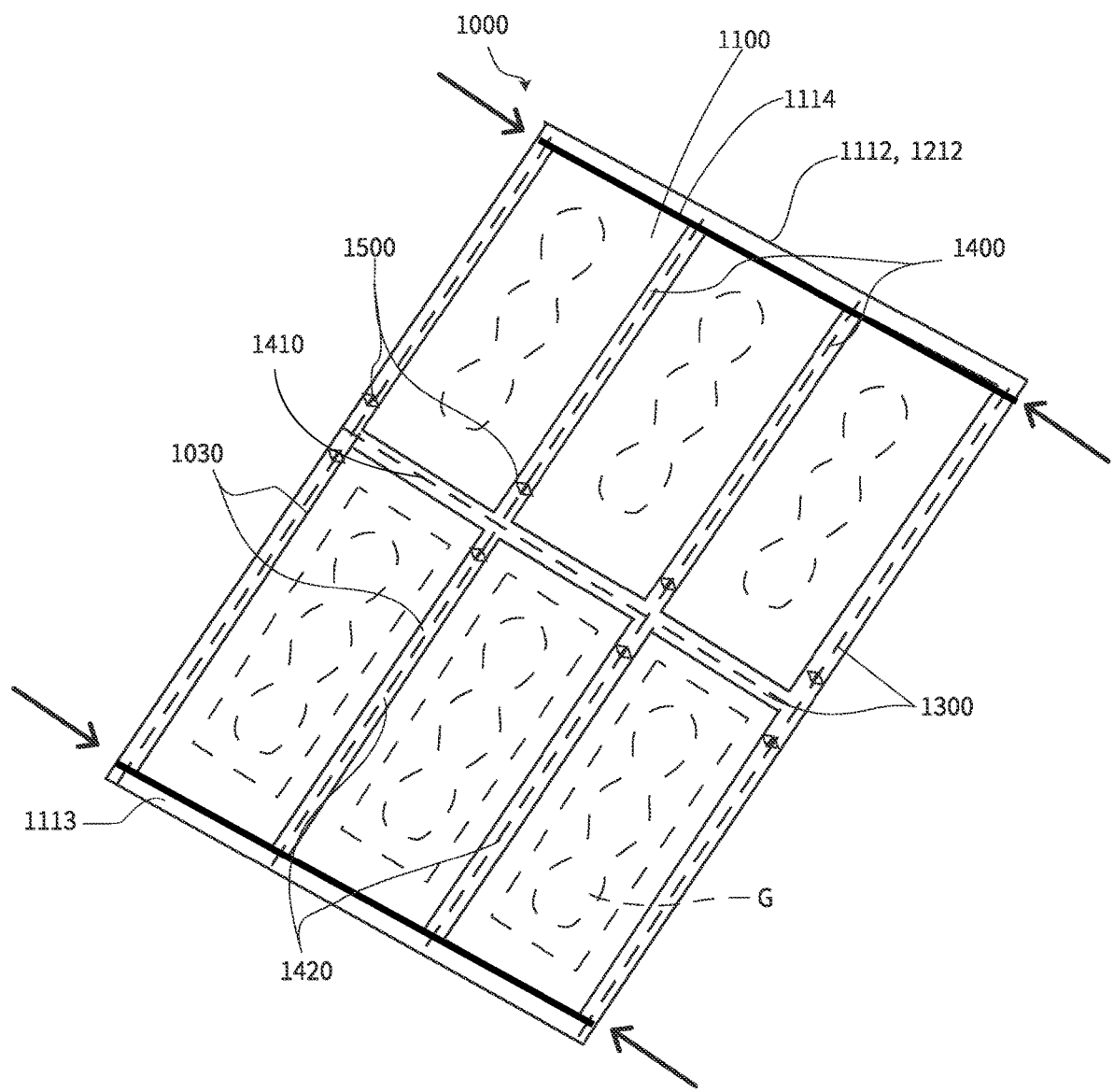
FIG. 2 is a schematic illustration of the multi-chamber container assembly of FIG. 1, in a second configuration.

The materials from which the first layer 1100 and the second layer 1200 are selected to ensure that the two layers can be joined to hermetically seal the storage volume 1060 within which the biological material G (or any other stored product described herein) is stored while also retaining the desired flexibility. The two layers 1100, 1200 can be joined together at the second end portion 1020 and along the side edges 1030 by any suitable mechanism, such as, for example, by heat bonding or by an adhesive. As shown in FIG. 2, the edge 1111 of the first layer 1100 and the edge 1211 of the second layer 1200 are configured to be joined together after the biological material G is loaded into the storage volume 1060 to form a closing seal 1113. In some embodiments, the closing seal 1113 is a permanent seal that is openable by destroying the seal and/or the layers 1100, 1200. In other embodiments, the closing seal 1113 is a peelable seal that is openable by separating the first layer 1100 from the second layer 1200 with a force that is less than a force required to tear or rip a material of the first layer 1100 and/or the second layer 1200. The peelable seal can be configured to have any suitable failure (or peel) mechanism and can be of any suitable peel strength.

As shown in FIG. 2, the edge 1112 of the first layer 1100 and the edge 1212 of the second layer 1200 are configured to be joined together after the biological material G (or any other stored product described herein) is loaded into another storage volume 1060 to form a closing seal 1114. In some embodiments, the closing seal 1114 is a permanent seal that is openable by destroying the seal and/or the layers 1100, 1200. For example, the closing seal 1114 can include a heat seal between layer 1100 and layer 1200. In other embodiments, the closing seal 1113 is a peelable seal that is openable by separating the first layer 1100 from the second layer 1200 with a force that is less than a force required to tear or rip a material of the first layer 1100 or the second layer 1200. The peelable seal can be configured to have any suitable failure (or peel) mechanism and can be of any suitable peel strength.

Figure 3:
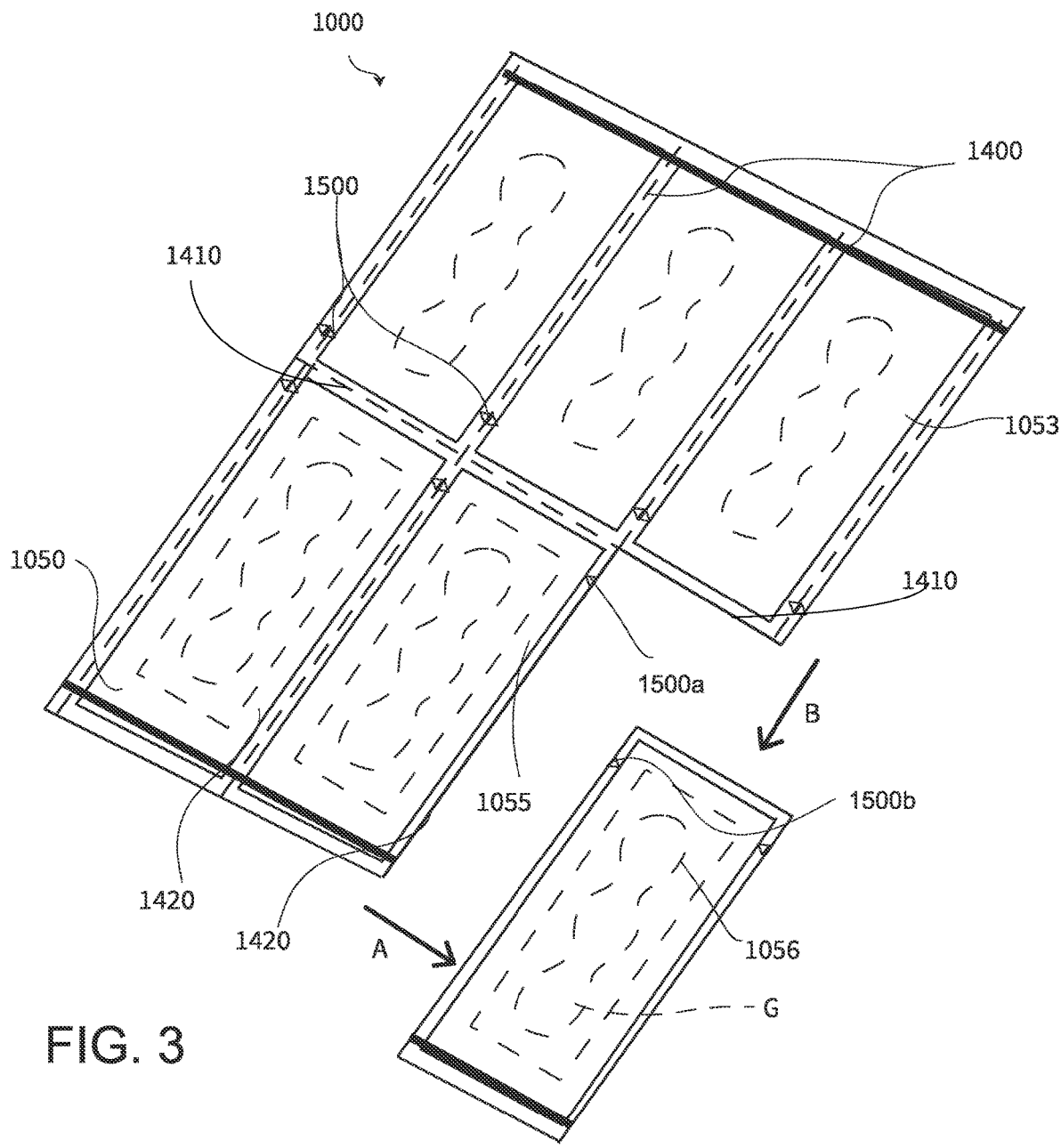
FIG. 3 is a schematic illustration of the multi-chamber container assembly of FIG. 1, in a third configuration.

In some embodiments, the multi-chamber container assembly 1000 includes a volume separating frangible region 1400. The volume separating frangible region 1400 is a region that facilitates the separation of one separable flexible container (e.g., 1056) from one or more other flexible containers (e.g., 1055 and/or 1053) as shown in FIG. 3. The frangible region 1400 can include perforations, thinning of material, stress risers suitable to directional tearing, adhesive attached otherwise detached containers or any other suitable mechanism for separating portions of the container assembly 1000 layers from one another. In some embodiments, the container assembly 1000 can include one or more longitudinal perforations 1410 positioned longitudinally between container volumes (e.g., between 1051, 1052, 1053 and 1054, 1055, 1056) shown in FIGS. 1-3. In some embodiments, the container assembly 1000 can include one or more transverse perforations 1420 positioned transversely between containers (e.g., between 1051, 1054 and 1052, 1055 and/or 1052, 1053, 1056) shown in FIGS. 1-3. In some embodiments, one or more of longitudinal perforations 1410 or the transverse perforations 1420 can be formed together with the seals 1300 or formed separately after the seals 1300 have been produced.

Figure 12:
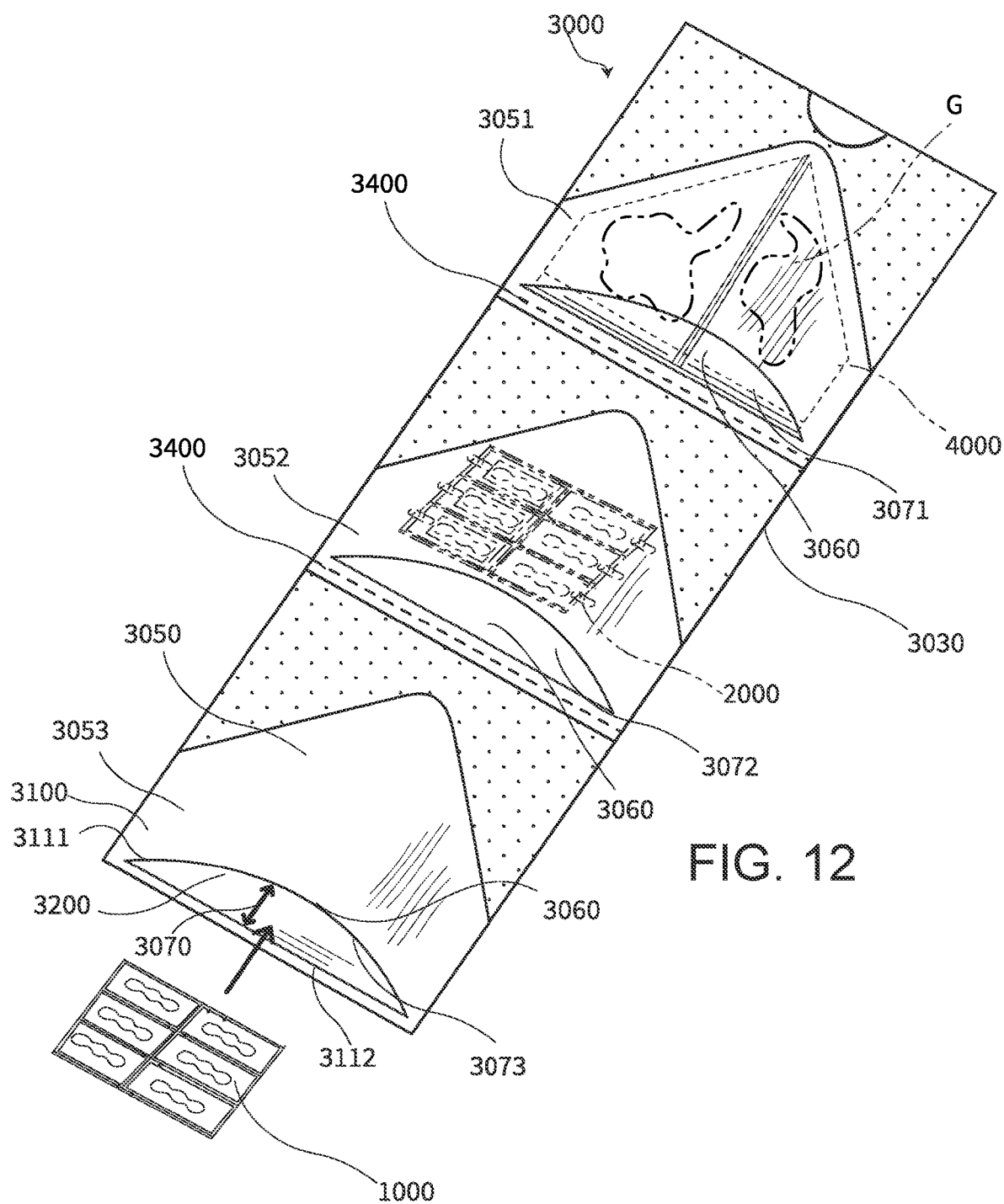
FIG. 12 is a schematic illustration of a multi-chamber container assembly, in a first configuration, according to an embodiment.

As shown in FIG. 3, the frangible regions are separated and a flexible container (e.g., flexible container 1056) is removable from the container assembly 1000 without compromising the structure of the remaining flexible containers (e.g., flexible containers 1051-1055). The separation is shown by arrows A and B in FIG. 3. While the embodiment shown in FIGS. 1-2 show rectangular containers 1051-1056 separated by an H shaped seal and frangible region 1400 positioned therebetween. However, it will be appreciated that other shapes of the containers, seals, and frangible regions are applicable as well. For example, FIG. 12 illustrates a container assembly 4000 with trapezoidal shaped separable containers. In some embodiments, flat layers can be provided with minimal attachment and custom separable containers can be formed thereon. In some embodiments, provided herein, the two layers (e.g., 1100, 1200) can be provided as tubular material that is flattened forming two longitudinal connections between the layers on the flattened longitudinal edges of the tubular material (e.g., layflat tubular film).

As shown in FIGS. 4 and 5, in some embodiments, the container assembly 1000 includes a volume opening frangible region 1500. The volume opening frangible region 1500 is a region that facilitates the opening of the separable flexible containers 1050, 1051, 1052, 1053, 1054, 1055, 1056 into the container volume 1060. In various examples, as discussed above, the connection between the first layer 1100 and the second layer 1200 can be a peelable connection such that the frangible region includes areas in which the first layer 1100 and the second layer 1200 can be peeled apart after connection. Examples of peelable connections are discussed in more detail below. In other examples, the frangible region 1500 can be a stress concentration riser as illustrated in FIGS. 1-5. The stress concentration riser can include any suitable feature to initiate tear across the volume. As illustrated in FIGS. 1-5, the frangible region 1500 includes tick perforations at the edges of the volume 1060 with sharp points suitable to initiate a tear 1500F into the volume 1060. In some embodiments, the tick perforations forming the frangible region 1500 is a V-shaped perforation. In some embodiments, as shown in FIG. 3, two frangible regions 1500 are formed adjacent to each other during the formation of the seal 1300 or after the formation of the seal 1300. A first frangible region 1500*a* of the adjacent frangible regions is operable to open a first one of the separable flexible containers (e.g., separable flexible container 1056) and a second frangible region 1500*b* is operable to open a second one of the separable flexible containers (e.g., separable flexible container 1055).

The container assembly 1000 can include a fold line F1. By folding the container assembly 1000 along the fold line F1, each of the openings 1070, 1071, 1072, 1073, 1074, 1075, 1076 are brought into proximity with one another. This allows for the loading of biological material G (or any other stored product described herein) directly into the openings 1070, 1071, 1072, 1073, 1074, 1075, 1076 in close proximity to each other. This allows for quicker and safer loading of material with less risk of waste. In some embodiments, one or more of the separable flexible containers 1050, 1051, 1052, 1053, 1054, 1055, 1056 (and any other separable flexible containers described herein) can be used to store a label or other tracking information associated with the biological material G (or any other stored product described herein) stored in the remaining separable flexible containers 1050, 1051, 1052, 1053, 1054, 1055, 1056. For example, the label can include identification, tracking, and/or chain of custody information. In some embodiments, the fold line F1 is formed by a seal that extends between two separable flexible containers 1050, 1051, 1052, 1053, 1054, 1055, 1056. In some embodiments, the fold line F1 can be defined by the seal itself. In some embodiments, the fold line F1 can be defined by a line of perforations. In one example, the line of perforations can be placed specifically to facilitate the fold. In another example, the line of perforations can be placed for separating the adjacent separable flexible containers 1050, 1051, 1052, 1053, 1054, 1055, 1056 and also serve as a fold line F1. In some embodiments, the fold line F1 can be defined by the seal and a line of perforations. As shown in FIG. 1, the two portions of containers can rotate around F1 causing the container assembly 1000 to fold (e.g., fold into a V-shaped configuration or a tent-shaped configuration).

Figure 10:
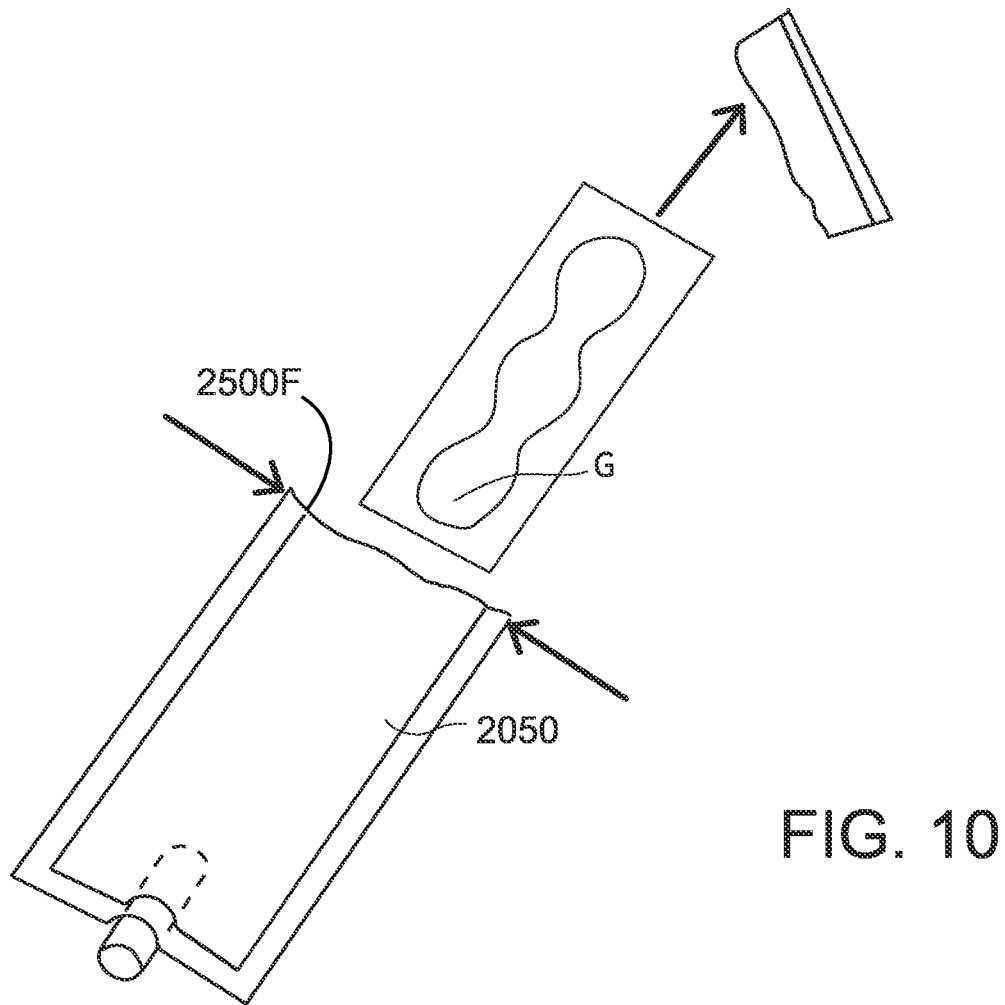
FIG. 10 is a schematic illustration of the multi-chamber container assembly of FIG. 6, in a fifth configuration.

FIGS. 6-10 are schematic illustrations of a multi-chamber container assembly 2000 (also referred to herein as container assembly) according to an embodiment. The container assembly 2000 is shown in a first (or open partially) configuration (FIG. 6), a second (or sealed) configuration (FIG. 7), a third (or separating) configuration (FIG. 8), a fourth (or separated) configuration (FIG. 9) and, a fifth (or open) configuration with the contents removed (FIG. 10). The container assembly 2000 (and any of the container assemblies described herein) can be used to store any of the tissue and biological materials described herein, and/or to perform any of the methods described herein, such as the method 10 of preparing a tissue specimen for storage (see FIG. 11) and/or the methods of rehydrating a tissue specimen for use in a procedure. As described herein, the container assembly 2000 provides a container that can be used for storage, transport, processing, and/or rehydration of a tissue specimen and/or biologic materials. The container assembly 2000 also includes a first layer 2100, a second layer 2200 and one or more seals 2300 connecting the first layer 2100 and the second layer 2200. The one or more seals 2300 for side edges and a center seam of separable, multiple separable flexible containers 2050, 2051, 2052, 2053, 2054, 2055, and 2056.

Figure 6:
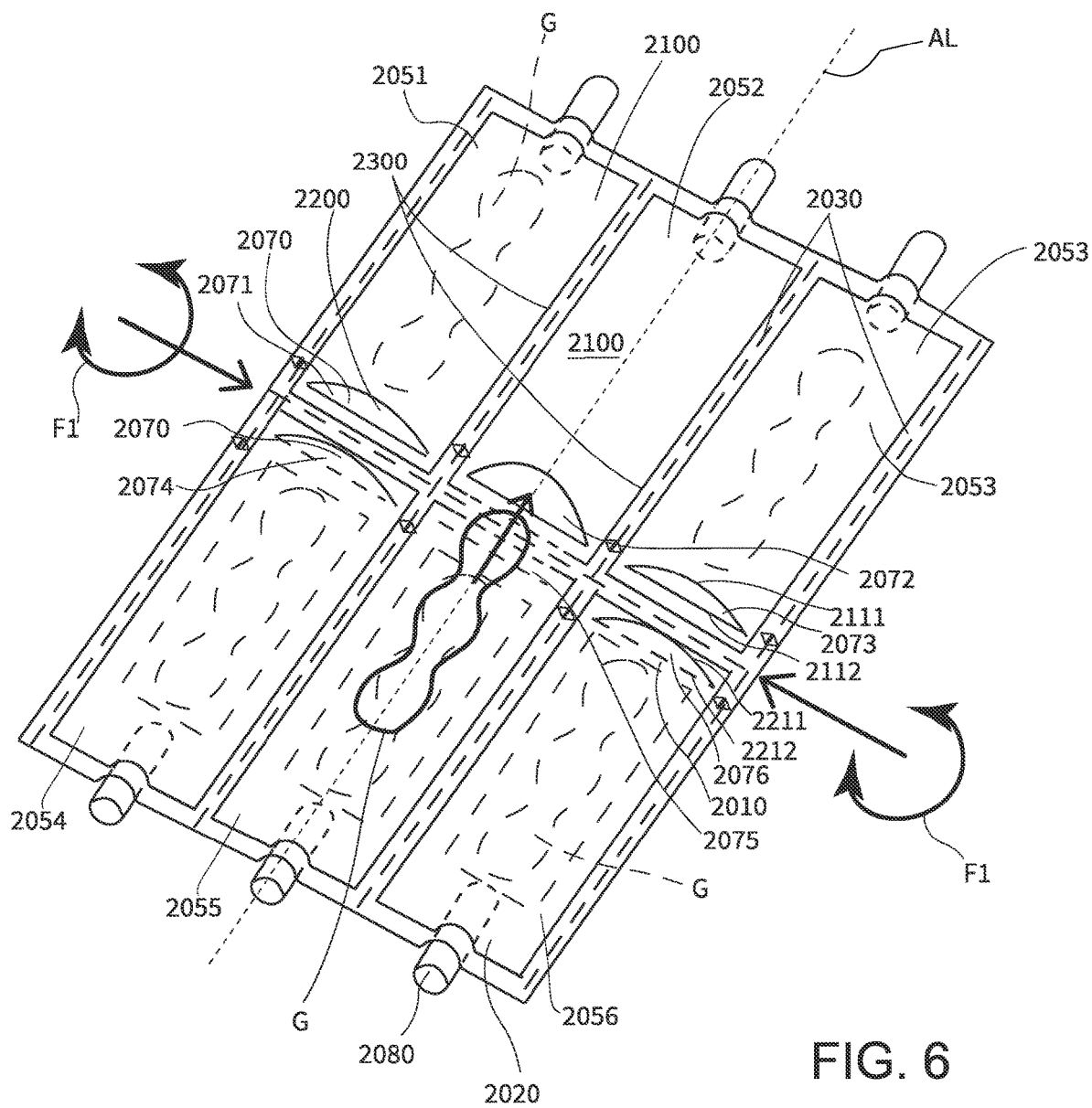
FIG. 6 is a schematic illustrations of a multi-chamber container assembly, in a first configuration, according to an embodiment.

Each of the multiple separable flexible containers 2050, 2051, 2052, 2053, 2054, 2055, 2056 includes a first end portion 2010, a second end portion 2020, and a pair of side edges 2030 between the first end portion 2010 and the second end portion 2020. The separable flexible container 2050, 2051, 2052, 2053, 2054, 2055, 2056 defines a longitudinal axis AL that extends longitudinally from the first end portion 2010 and the second end portion 2020. The separable flexible container 2050, 2051, 2052, 2053, 2054, 2055, 2056 is constructed from a first layer 2100 and a second layer 2200 coupled together to define a storage volume 2060. As shown in FIG. 6, when the container assembly 2000 is in the first (or opened) configuration, one or more edges (e.g., edges 2111 and/or 2112) of the first layer 2100 is spaced apart from one or more edges (e.g., edges 2211 and/or 2212) of the second layer 2200 to define a plurality of openings 2070 (e.g., opening 2071-2076) into the storage volume 2060 of each of the separable flexible containers 2050, 2051, 2052, 2053, 2054, 2055, 2056. The openings 2070, 2071, 2072, 2073, 2074, 2075, 2075, 2076 can be of any suitable size to facilitate loading of the tissue, biological material and/or treatment G (e.g., a tissue graft), as described herein. In some embodiments, a support structure 2600 is used to support the material G. In such embodiments, the opening 2070, 2071, 2072, 2073, 2074, 2072, 2075, 2076 can be a suitable size to facilitate the loading of the support structure. As shown in FIGS. 6-10, some materials G are supported and some are not. In some embodiments, the openings 2070 can extend across a portion of the length of an end or a side of the separable flexible container 2050, 2051, 2052, 2053, 2054, 2055, 2056. In other embodiments, the opening 2070 can extend across substantially all of the end or side of the separable flexible container 2050, 2051, 2052, 2053, 2054, 2055, 2056. As shown in FIGS. 6-10, the container assembly 2000 can include multiple openings 2070, 2071, 2072, 2073, 2074, 2075, 2075, 2076 along the center seam. In some embodiments, as illustrated in FIGS. 6-10, each of the multiple separable flexible containers 2050, 2051, 2052, 2053, 2054, 2055, 2056 includes a second opening 2080. In some embodiments, the second opening 2080 is a port. For example, as shown in FIGS. 6-10, the two layers 2100, 2200 respectively are joined at the second end portion 2020 with the port 2080 therebetween, and the two side edges 2030 are joined together. The port 2080 is coupled to the second end portion 2020 of the container assembly 2000 and is configured to allow fluid communication between a volume outside of the container assembly 2000 and the storage volume 2060. Thus, the port 2080 can be used to provide access to the storage volume 2060 and the tissue specimen G after the first end portion 2010 has been sealed closed. In this manner, the tissue specimen G can be treated with a preservation fluid or other material after being sealed into the container assembly 2000. The port 2080 can also be coupled to a vacuum source to evacuate the storage volume for storage of the tissue specimen G. Moreover, during a surgical procedure, the port 2080 can allow for inflow of rehydration fluid.

The port 2080 can be any suitable port that selectively provides fluid communication to the storage volume 2060. For example, the port 2080 can include a tube, a valve, and/or a cap. In some embodiments, the port 2080 can be a needle-free port. In some embodiments, the port 2080 can be a swabable connector. Similarly stated in some embodiments, the port 2080 can have external surfaces and can be devoid of recesses or crevices such that the port 2080 can be easily wiped or "swabbed" to maintain sterility during use. In some embodiments, the port 2080 can include any of the barbed, swabable valves produced by the Halkey-Roberts Corporation, such as the 2455 series of swabable valves. In other embodiments, the port 2080 (and any of the ports described herein) need not be either a swabable connector or a needle-free port; any suitable port can be employed. In some embodiments, the port 2080 can include a male or female luer fitting.

Although the port 2080 is shown as being coupled at the second end portion 2020 of the separable flexible container 2050, 2051, 2052, 2053, 2054, 2055, 2056, in other embodiments, the port 2080 (and any of the ports described herein) can be coupled at any location and to any portion of the separable flexible container 2050, 2051, 2052, 2053, 2054, 2055, 2056. For example, in some embodiments, the port 2080 (and any of the ports described herein) need not be coupled to an end of the container that is opposite from the end of the container that includes the peelable seal. The port 2080 (and any of the ports described herein) can be offset from a center line of the separable flexible container 2050, 2051, 2052, 2053, 2054, 2055, 2056. For example, in some embodiments, the port can be located at a corner of the separable flexible container, 2051, 2052, 2053, 2054, 2055, 2056. Moreover, the in some embodiments, the port 2080 (and any of the ports described herein) can be coupled in a central portion of the separable flexible container 2050, 2051, 2052, 2053, 2054, 2055, 2056.

While shown in FIGS. 6-10 with opposing openings on a single container 2050 and shown in FIGS. 1-5 with a single opening on each separable flexible containers 1050, 1051, 1052, 1053, 1054, 1055, 1056, in some embodiments, the container assembly 2000 can include a combination of the separable flexible containers of FIGS. 1-5 (with open ends) and the separable flexible containers of FIGS. 6-10 (with ported ends). In this way some containers of the container assembly 2000 will have multiple openings and some will not. In other embodiments, additional container combinations, shapes, sizes and contents can be included in the container assembly 2000. For example, although the container assembly 2000 is shown with rectangularly-shaped separable flexible containers, any of the container assemblies described herein can include separable flexible containers with perimeters of other shapes, including but not limited to, square, triangle, trapezoid, or funnel shapes. In some embodiments, the seal 2300 of the container assembly 2000 (or seals of any of the container assemblies described herein) can formed as a linear and/or curvilinear form such that an internal volume of a corresponding separable flexible container 2050, 2051, 2052, 2053, 2054, 2055, 2056 includes a circular or curved boundary.

The first and second layers 2100, 2200 respectively can be constructed of any suitable material. The first layer 2100 can have a first stiffness and the second layer 2200 can have a second stiffness. In some embodiments, the stiffnesses are the same. In some embodiments the stiffnesses are different. In some embodiments the second stiffness is greater than the first stiffness. In some embodiments, the first stiffness is greater than the second stiffness. In some embodiments, the layers 2100, 2200 respectively can constructed from the same material. In other embodiments, the layers 2100, 2200 respectively can be constructed from a different material and the second stiffness can be different than the first stiffness. In some embodiments, the first layer 2100 can be a thin, peelable film. The first layer 2100 can have any suitable thickness to provide the desired strength, flexibility, and sealing characteristics. For example, in some embodiments, the first layer 2100 can be between about 10 microns (0.010 mm) and about 2000 microns (2.0 mm). In some embodiments, the first layer 2100 can be between about 50 microns (0.050 mm) and about 200 microns (0.200 mm). In other embodiments, the first layer can be between about 50 microns (0.050 mm) and about 1000 microns (0.100 mm). The second layer 2200 can have any suitable thickness to provide the desired strength, flexibility, and sealing characteristics. For example, in some embodiments, the second layer 2200 can be between about 10 microns (0.010 mm) and about 2000 microns (2.0 mm). In some embodiments, the second layer 2200 can be between about 50 microns (0.050 mm) and about 200 microns (0.200 mm). In other embodiments, the second layer 2200 can be between about 50 microns (0.050 mm) and about 1000 microns (0.100 mm).

In some embodiments, the layers 2100, 2200 of the container assembly 2000 (or the material of any of the container assemblies described herein) can be produced out of any one or more of the following materials: polyethylene (PE), low density polyethylene (LDPE), composites of LDPE, linear low-density polyethylene (LLDPE), high density poly ethylene (HDPE), polychlorotrifluoroethylene (PCTFE), ethylene tetrafluoroethylene (ETFE), polytetrafluoroethylene (PTFE), fluorinated ethylene propylene (FEP), polyurethane, polyimides (coats or non-coated), polyvinyl chloride (PVC), perfluoroalkoxy alkane (PFA), ethylene-vinyl acetate (EVA), polyvinylidene fluoride or polyvinylidene difluoride (PVDF), THV (a polymer of tetrafluoroethylene, hexafluoropropylene and vinylidene fluoride), PFE (Poly(fluorenylene ethynylene)), nylon, and/or composite of nylon. In some embodiments, any of the multi-chamber packaging using the materials above can be co-extruded and/or laminated. In some embodiments, any of the multi-chamber packaging using the materials above can further include aluminum foil laminate, aluminum oxide laminate, or laminated or co-extruded with aluminum oxide. In some embodiments, any of the multi-chamber container assemblies can be laminated with a layer of alder or any other suitable adhesive. In some embodiments, the material of the first layer 2100 and the material second layer 2200 are the same. In other embodiments, the material of the first layer 2100 is different from the material of the second layer 2200. For example, the material and/or thickness of the second layer 2200 may be selected such that a rigidity of the second layer 2200 is greater than the rigidity of the first layer 2100.

Figure 7:
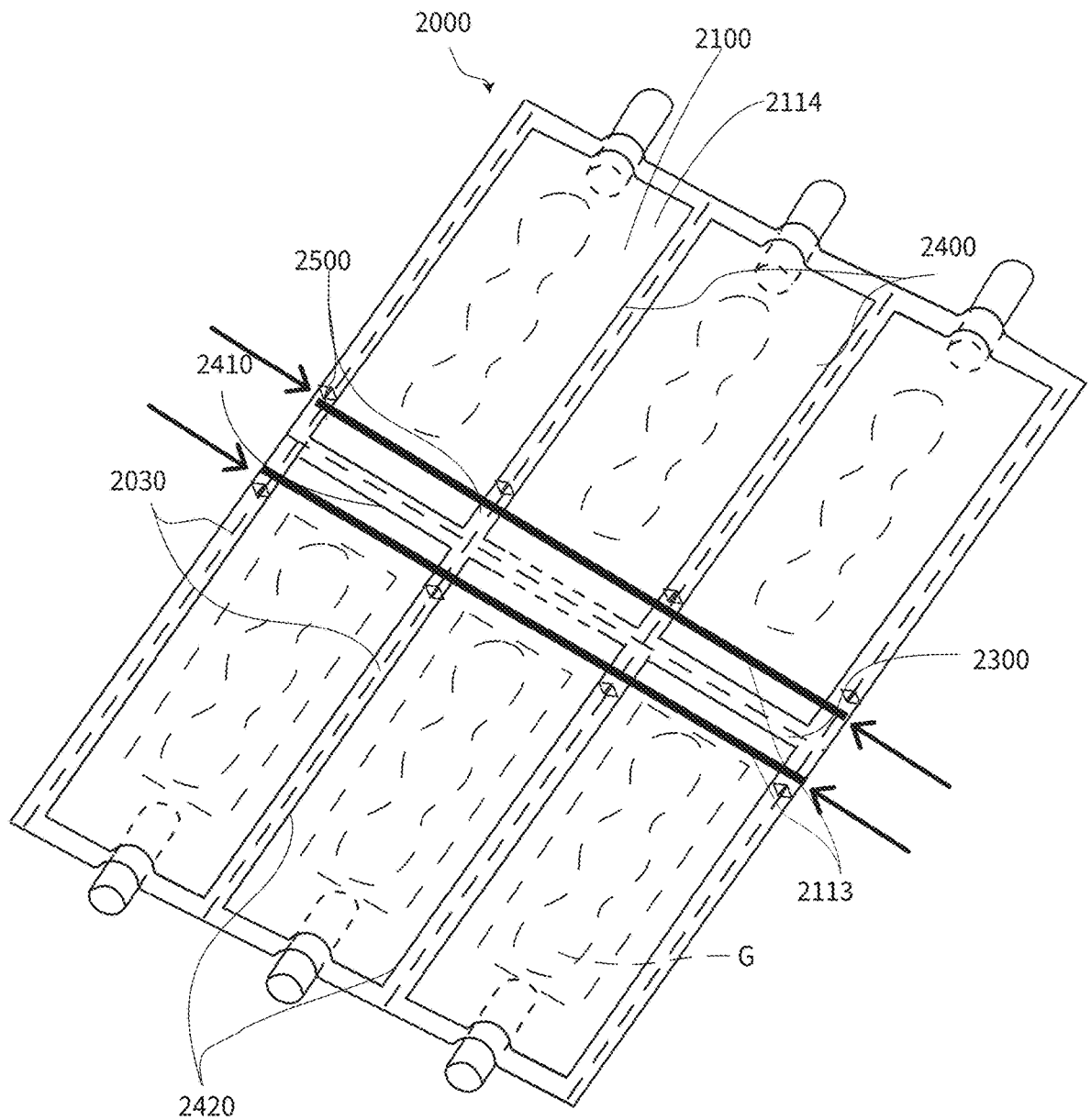
FIG. 7 is a schematic illustration of the multi-chamber container assembly of FIG. 6, in a second configuration.

The materials from which the first layer 2100 and the second layer 2200 are selected to ensure that the two layers 2100, 2200 can be joined to hermetically seal the storage volume 2060 within which the biological material G (or any other stored product described herein) is stored while also retaining the desired flexibility. The two layers 2100, 2200 can be joined together at the second end portion 2020 and along the side edges 2030 by any suitable mechanism, such as, for example, by heat bonding or by an adhesive. As shown in FIG. 7, the edge 2111 of the first layer 2100 and the edge 2211 of the second layer 2200 are configured to be joined together after the biological material G is loaded into the storage volume 2060 to form a closing seal 2113. In some embodiments, the closing seal 2113 is a permanent seal that is openable by destroying the seal and/or the layers 2100, 2200. In other embodiments, the closing seal 2113 is a peelable seal that is openable by separating the first layer 2100 from the second layer 2200 with a force that is less than a force required to tear or rip a material of the first layer 2100 or the second layer 2200. The peelable seal can be configured to have any suitable failure (or peel) mechanism and can be of any suitable peel strength.

As shown in FIG. 6, the edge 2112 of the first layer 2100 and the edge 2212 of the second layer 2200 are configured to be joined together after the biological material G is loaded into another storage volume 2060 to form a closing seal 2114. In some embodiments, the closing seal 2114 is a permanent seal that is openable by destroying the seal and/or the layers 2100, 2200. For example, the closing seal 2114 can include a heat seal between layer 2100 and layer 2200. In other embodiments, the closing seal 2113 is a peelable seal that is openable by separating the first layer 2100 from the second layer 2200 with a force that is less than a force required to tear or rip a material of the first layer 2100 or the second layer 2200. The peelable seal can be configured to have any suitable failure (or peel) mechanism and can be of any suitable peel strength.

Figure 8:
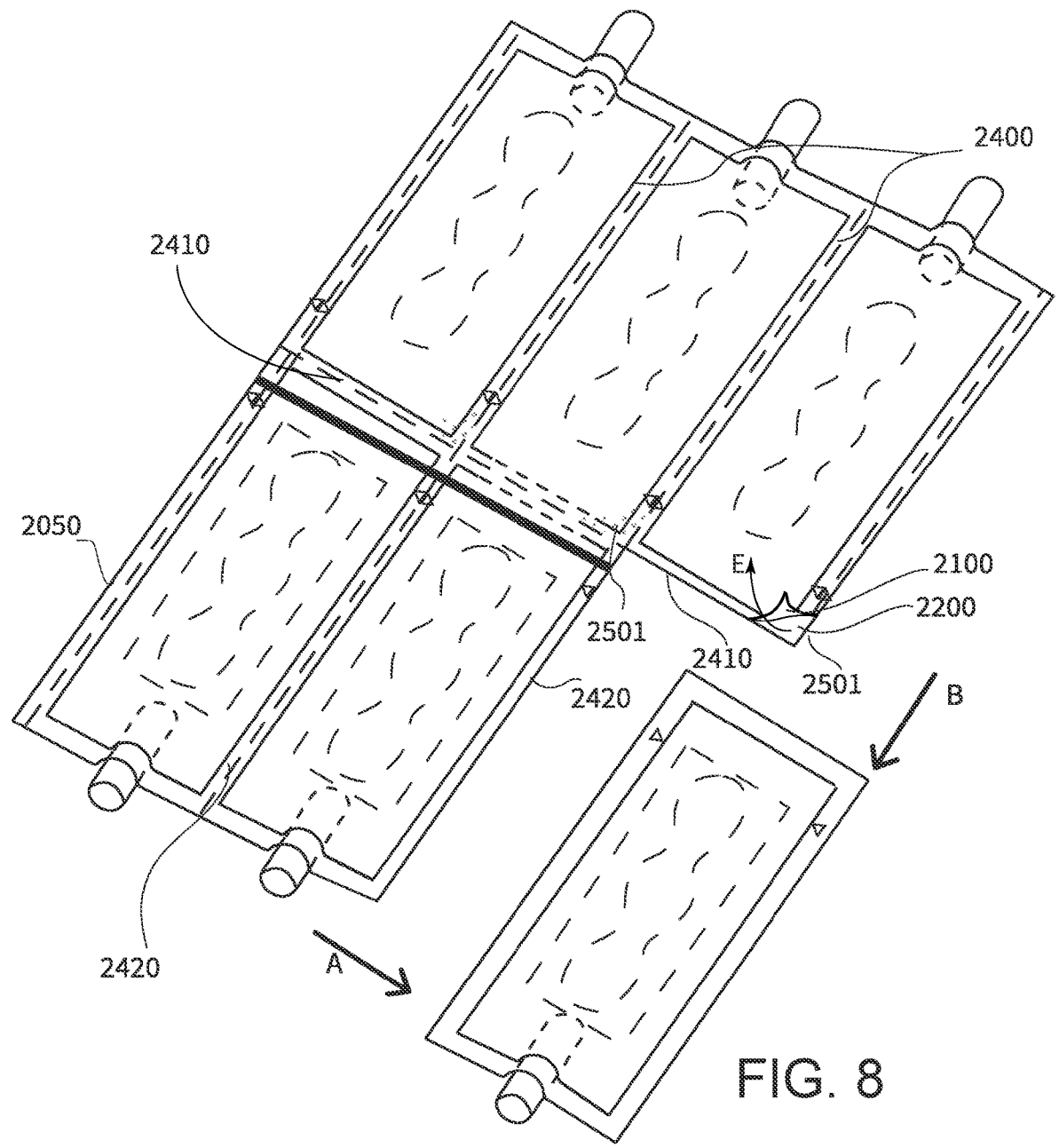
FIG. 8 is a schematic illustration of the multi-chamber container assembly of FIG. 6, in a third configuration.
Figure 9:
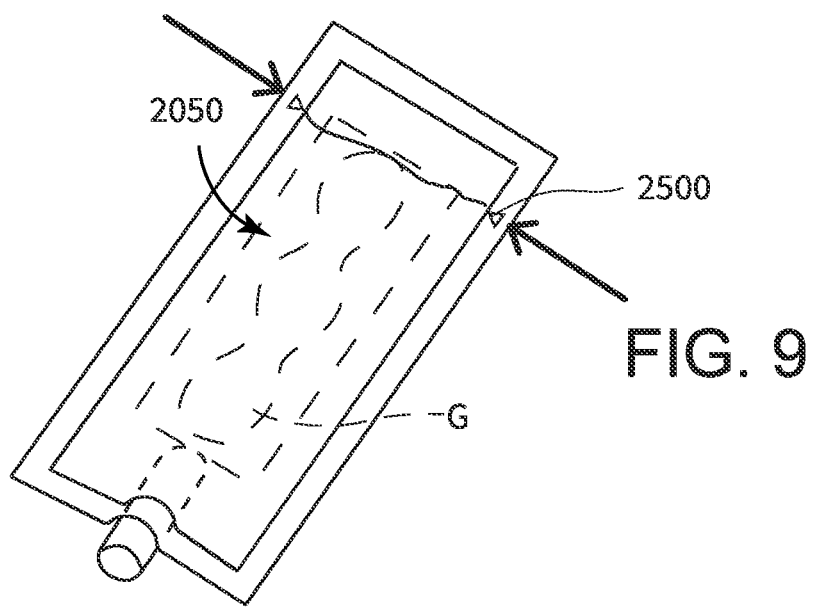
FIG. 9 is a schematic illustration of the multi-chamber container assembly of FIG. 6, in a fourth configuration.

In some embodiments, the multi-chamber container 2000 includes a volume separating frangible region 2400. The volume separating frangible region 2400 is a region that facilitates the separation of one separable flexible container (e.g., 2056) from one or more other separable flexible containers (e.g., 2055 and/or 2053) as shown in FIG. 8. The frangible region 2400 can include perforations, thinning of material, stress risers suitable to directional tearing, adhesive attached otherwise detached containers or any other suitable mechanism for separating portions of the container assembly 2000 layers from one another. In some embodiments, the container assembly 2000 can include one or more longitudinal perforations 2410 positioned longitudinally between container volumes (e.g., between 2051, 2052, 2053 and 2054, 2055, 2056) shown in FIGS. 6-8. In some embodiments, the container assembly 2000 can include one or more transverse perforations 2420 positioned transversely between containers (e.g., between 2051, 2054 and 2052, 2055 and/or 2052, 2055 and 2053, 2056) shown in FIGS. 6-8. As shown in FIG. 8, the frangible regions are separated and a flexible container (e.g., flexible container 2056) is removable from the flexible container assembly 2000 without compromising the structure of the remaining flexible containers (e.g., flexible containers 2051-2055). The separation is shown by arrows A and B in FIG. 8. While the embodiment shown in FIGS. 6-7 show rectangular containers 2051-1056 separated by an H shaped seal and frangible region 2400 positioned therebetween. However, it will be appreciated that other shapes of the containers, seals, and frangible regions are applicable as well. For example, FIG. 12 illustrates a container assembly 4000 with trapezoidal shaped separable containers. In some embodiments, flat layers can be provided with minimal attachment and custom separable containers can be formed thereon. In some embodiments, provided herein, the two layers (e.g., 2100, 2200) can be provided as tubular material that is flattened forming two longitudinal connections between the layers on the flattened longitudinal edges of the tubular material (e.g., layflat tubular film).

In some embodiments, the separable flexible container assembly 2000 includes a volume opening frangible region 2500. The volume opening frangible region 2500 is a region that facilitates the opening of the separable flexible container 2050, 2051, 2052, 2053, 2054, 2055, 2056 into their respective container volumes 2060. In various examples, as discussed above, the connection between the first layer 2100 and the second layer 2200 can be a peelable connection such that the frangible region includes areas in which the first layer and the second layer can be peeled apart after connection. For example, FIG. 8 illustrates a frangible region 2500 including a peelable separation region 2501. The peelable separation region 2501 allows for the separation of the first layer 2100 and the second layer 2220. The initiation of this peel allows for the two layers to be at least partially separated and in some embodiments entirely separated. Other examples of peelable connections are discussed in more detail below with reference to the embodiments shown in FIGS. 12-15. The examples of peelable separation regions shown in FIGS. 12-15 are applicable to the embodiments shown in FIGS. 6-10. In other examples, the frangible region 2500 can be a stress concentration riser as illustrated in FIGS. 6-10. The stress concentration riser can include any suitable feature to initiate tear across the volume. As illustrated in the embodiments of FIGS. 6-10, this can include tick perforations at the edges of the volume 2060 with sharp points suitable to initiate a tear 2500F into the volume 2060. In some embodiments, the tick perforations forming the frangible region 2500 is a V-shaped perforation. In some embodiments, as shown in FIG. 8, two frangible regions 2500 are formed adjacent to each other during the formation of the seal 2300 or after the formation of the seal 2300. A first frangible region 2500a of the adjacent frangible regions is operable to open a first one of the separable flexible containers (e.g., separable flexible container 2056) and a second frangible region 2500b is operable to open a second one of the separable flexible containers (e.g., separable flexible container 2055).

In accordance with some embodiments, the container 2050 can include features of the various the containers as disclosed in Patent Pub. No. 2020/008921 (the '921 patent), titled "Sample Container with Peelable Seal and Access Port," which is hereby incorporated by reference in its entirety. In light of the disclosure in the present application a person of ordinary skill in the art could adapt the features of the container in the '921 reference to be formed on as a container assembly having frangible regions forming an assembly with a plurality those or other containers as discussed herein.

In accordance with some embodiments, the container 2050 can include features of the various the containers as disclosed in Patent Pub. No. 2020/008921 (the '921 patent), titled "Sample Container with Peelable Seal and Access Port," which is hereby incorporated by reference in its entirety. In light of the disclosure in the present application a person of ordinary skill in the art could adapt the features of the container in the '921 reference to be formed on as a container assembly having frangible regions forming an assembly with a plurality those or other containers as discussed herein.

Figure 11:
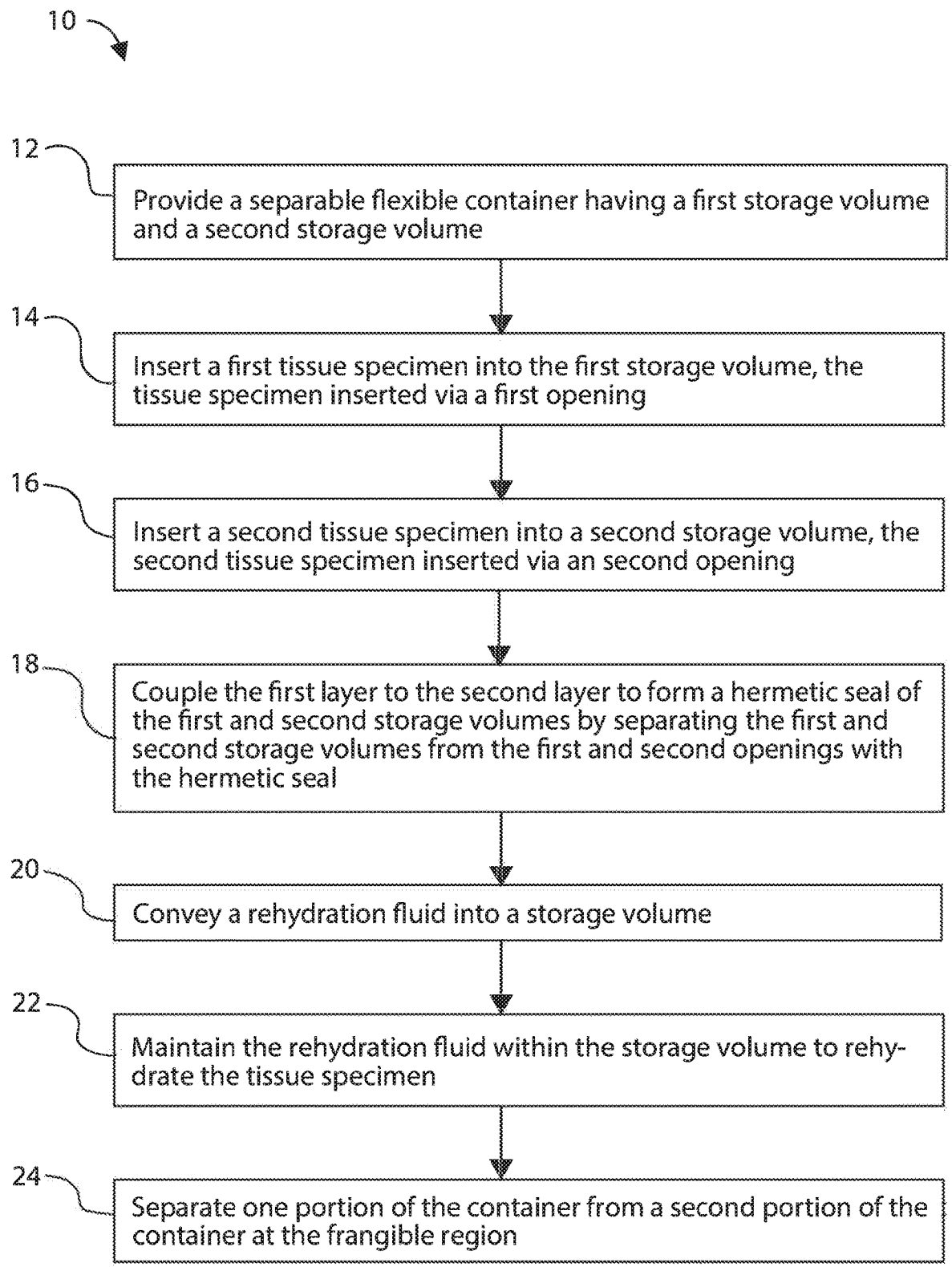
FIG. 11 is a flow diagram of a method of preparing a tissue specimen for storage according to an embodiment.

In some embodiments, the container assemblies discussed herein (e.g., assembly 1000 and 2000) and their variants can be used to store the biological material G (in addition to other types of materials as discussed below). FIG. 11 illustrates a flow chart showing a method 10 for utilizing the separable flexible container assembly for the packaging of biological material. Although the method 10 is described with reference to the container assemblies 1000 and 2000, the method 10 can be performed with other suitable containers assemblies described herein. The container assembly (e.g., 1000 and 2000) includes a first storage volume defined between a first layer of the flexible container and a second layer of the flexible container. A second storage volume defined between the first layer of the flexible container and the second layer of the flexible container is also provided at 12. A first tissue specimen is inserted into the first storage volume via a first opening defined by at least one of separated portions of the first layer with edges that are able to be spaced apart providing external access to the first storage volume at 14. External access to the first storage volume is provided by separated portions of the layers (e.g., separated first layer and second layer or separated portions of one of the layers). A second tissue specimen is inserted into a second storage volume defined between the first layer and the second layer of the flexible container at 16. The first layer is coupled to the second layer to form a hermetic seal of the first and second storage volumes at 18. This separates the first and second storage volumes from the first and second openings with the hermetic seal. From this point in the process the biological materials G can be stored. In some embodiments, the container assemblies are further packaged into separate volumes within an overwrap container assembly before storage.

When used, the packaged biological materials G is allocated. In some embodiments, the container assemblies are extracted from the overwrap by peeling back the top layer of the overwrap exposing as much of the biological material G is to be used. In some embodiments, rehydration fluid is injected through the port into the storage volume (see container assembly 2000.) at 20. The fluid is maintained in the volume for enough time to rehydrate the material G at 22. The portions of the container assembly to be used are separated from one another and opened via their respective frangible regions (e.g., peel or tear). The biological material G can then be used in its medical procedure.

Figure 13:
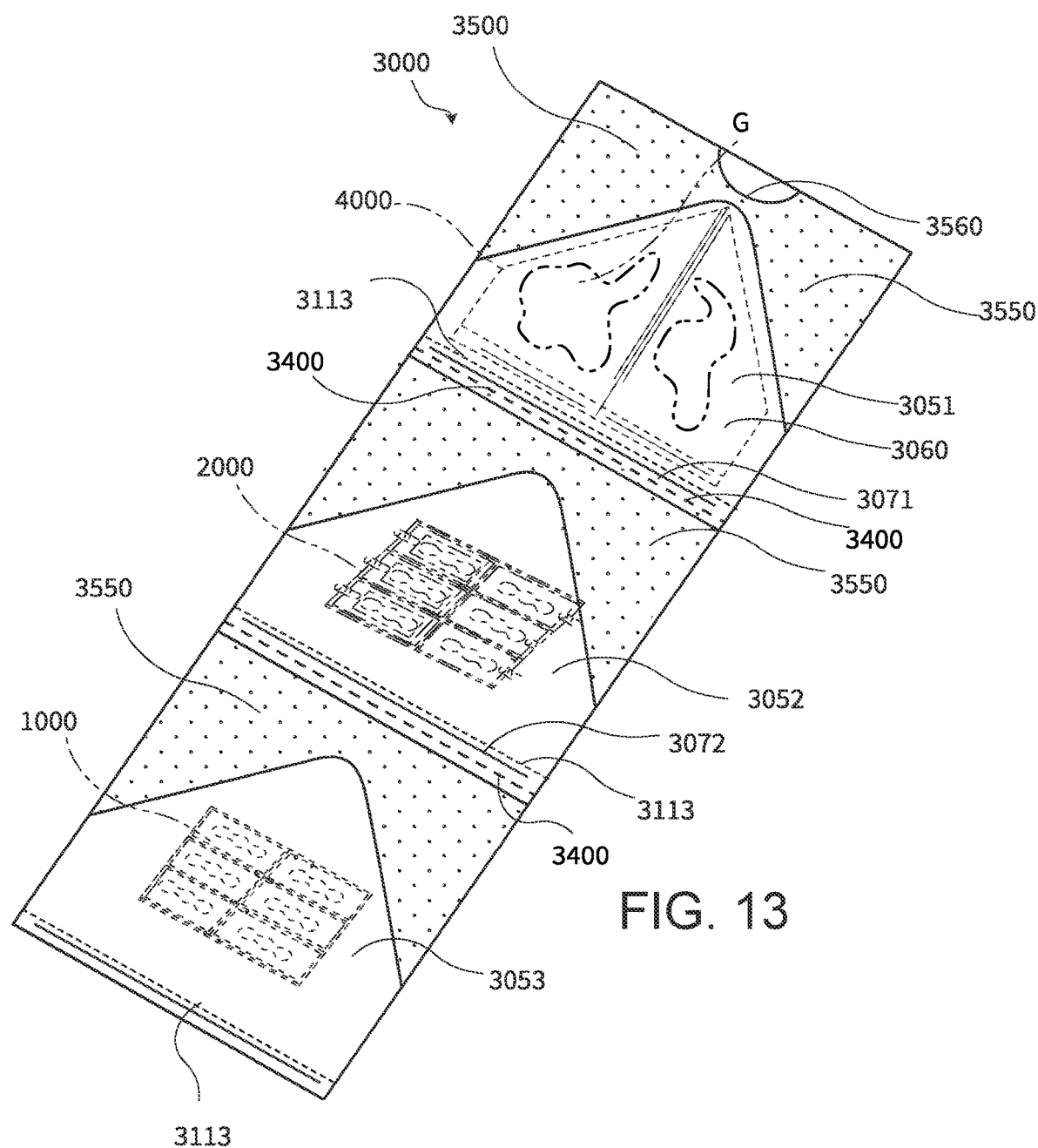
FIG. 13 is a schematic illustration of the multi-chamber container assembly of FIG. 12, in a second configuration.
Figure 14:
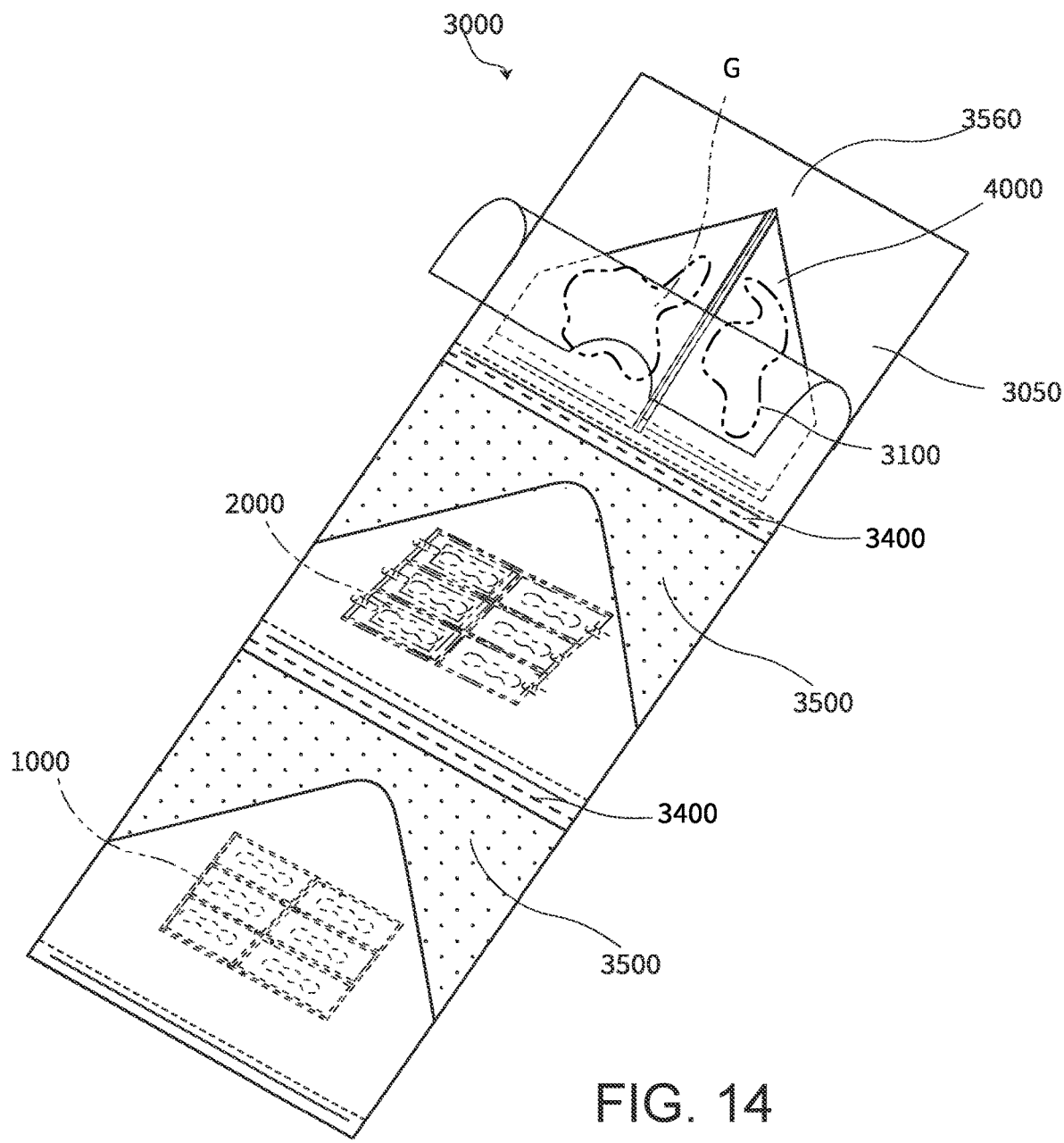
FIG. 14 is a schematic illustration of the multi-chamber container assembly of FIG. 12, in a third configuration.
Figure 15:
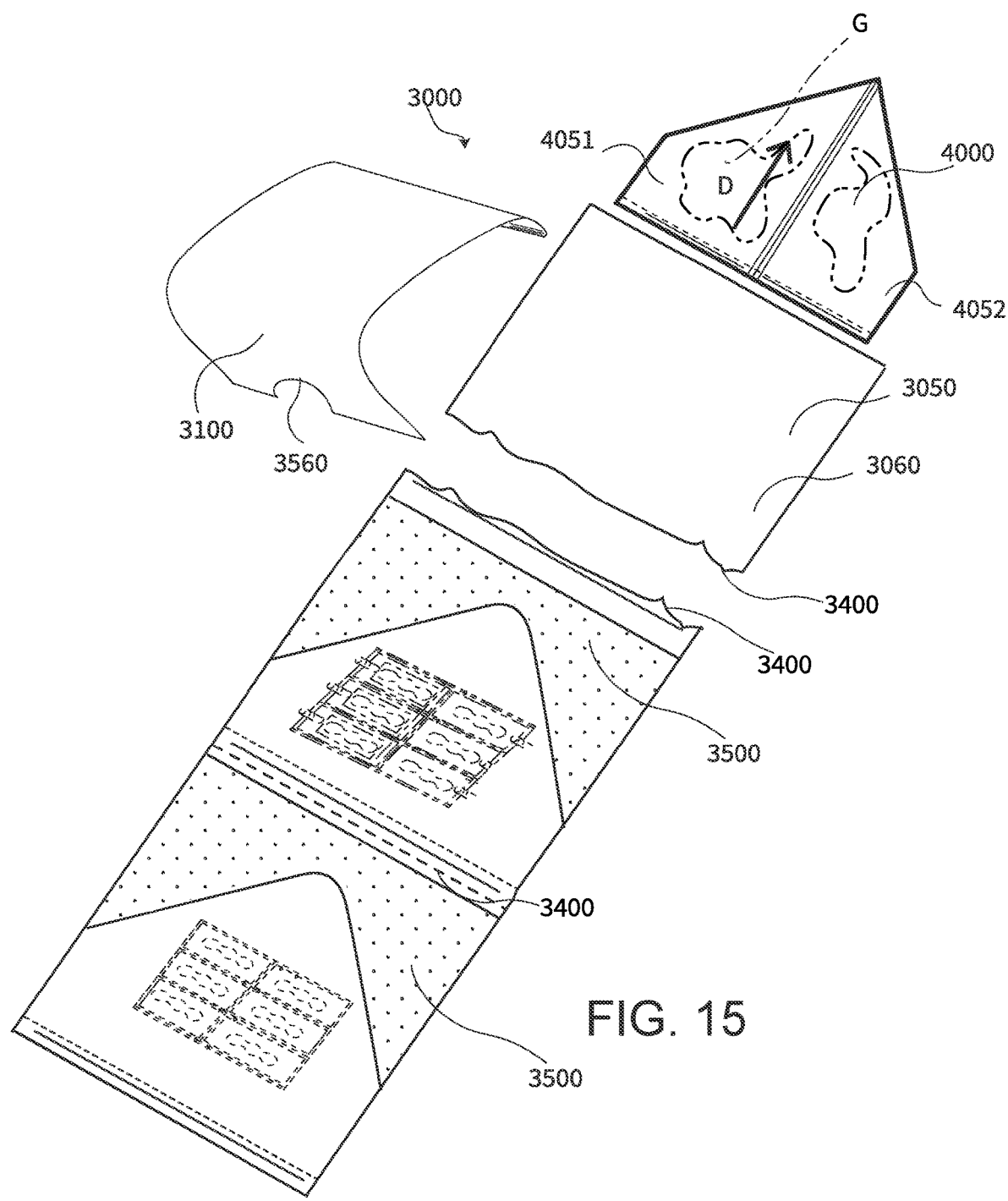
FIG. 15 is a schematic illustration of the multi-chamber container assembly of FIG. 12, in a fourth configuration.

FIGS. 12-15 are schematic illustrations of a multi-chamber overwrap assembly 3000 (also referred to as overwrap assembly or container overwrap assembly) according to an embodiment. The overwrap assembly 3000 is shown in a first (or open partially) configuration (FIG. 12), a second (or sealed) configuration (FIG. 13), a third (or opening) configuration (FIG. 14), and a fourth (or separated) configuration (FIG. 15). The overwrap assembly 3000 (and any of the container assemblies described herein) can be used to perform any of the methods described herein, such as the method 10 of preparing a tissue specimen for storage (see FIG. 11) and/or the methods of rehydrating a tissue specimen for use in a procedure (see incorporated reference above). As described herein, the overwrap assembly 3000 provides an outer container that can be used for storing and protecting a single-chamber container or a multi-chamber container (such as the multi-chamber contain assemblies described herein) used to store tissue and/or biologic materials. While the single-chamber containers or the multi-chamber containers used for storing tissue and/or biologic materials require that these containers be produced with biologically inert materials, the overwrap assembly 3000 can be produced with other materials to ensure that the overwrap remain stable, flexible and optically clear from ambient temperature to temperatures below 200° C.

In the embodiment shown in FIGS. 12-14, the overwrap assembly 3000 encloses other containers or packages containing tissue and/or biological material, such as the biological materials described herein. None-the-less, in other embodiments, the structures shown in FIGS. 12-14 can be used to directly store the biological materials G, or any of the stored products described herein. As shown, the overwrap assembly 3000 includes separable multiple separable flexible containers 3050, 3051, 3052, 3053. The overwrap assembly 3000 also includes a first layer 3100, a second layer 3200 and one or more seals 3300 connecting the first layer 3100 and the second layer 3200. The separable flexible container 3050, 3051, 3052, 3053 is constructed from a first layer 3100 and a second layer 3200 coupled together to define a storage volume 3060. As shown in FIG. 1, when the overwrap assembly 3000 is in the first (or opened) configuration, one or more edges (e.g., edges 3111 and/or 3112) of the first layer 3100 is spaced apart from one another to define a plurality of openings 3070 (e.g., openings 3071, 3072, 3073) into the storage volume 3060 of each of the separable flexible containers 3050, 3051, 3052, 3053. In other embodiments, these edges could be spaced apart from one or more edges (e.g., edges 3211 and/or 3212) of the second layer 3200 to define a plurality of openings 3070 (e.g., openings 3071, 3072, 3073) into the storage volume 3060 of each of the separable flexible containers 3050, 3051, 3052, 3053. The openings 3070 (e.g., openings 3071, 3072, 3073) can be of any suitable size to facilitate loading of the containers of biological material G. In some embodiments, the opening 3070 can extend across a portion of the length of an end or a side of the separable flexible container 3050, 3051, 3052, 3053. In other embodiments, the opening 3070 can extend across substantially all of the end or side of the separable flexible container 3050, 3051, 3052, 3053. As shown in FIGS. 12-16, the overwrap assembly 3000 can include multiple openings along multiple edges. However, in the embodiment shown in FIG. 12. The openings 3070 all face the same way toward an adjacent edge of the respective separable flexible container 3050, 3051, 3052, 3053.

In some embodiments, the overwrap assembly 3000 can include multiple separable flexible containers 3050, 3051, 3052, 3053. Such an embodiment is illustrated with a single flexible container assembly within a separable flexible container shown in FIGS. 12-15. The overwrap assembly 3000 also can include one or more of the features, characteristics and/or components discussed with regards to any one or more of the multiple separable flexible containers discussed herein.

The first and second layers 3100, 3200 respectively can be constructed of any suitable material for the storage of biological material G or the containers storing biological material G. In some embodiments, the layers 3100, 3200 respectively can constructed from the same material. In other embodiments, the layers 3100, 3200 respectively can be constructed from a different material and the second stiffness can be different than the first stiffness. In some embodiments, the first layer 3100 can be a thin, peelable film. The first layer 3100 can have any suitable thickness to provide the desired strength, flexibility, and sealing characteristics. For example, the first layer 3100 can be between about 10 microns (0.010 mm) and about 2000 microns (2.0 mm). In some embodiments, in some embodiments, the first layer 3100 can be between about 50 microns (0.050 mm) and about 200 microns (0.200 mm). In other embodiments, the first layer can be between about 50 microns (0.050 mm) and about 3000 microns (0.100 mm). The second layer 3200 can have any suitable thickness to provide the desired strength, flexibility, and sealing characteristics. For example, in some embodiments, the second layer 3200 can be between about 10 microns (0.010 mm) and about 2000 microns (2.0 mm). In some embodiments, the second layer 3200 can be between about 50 microns (0.050 mm) and about 200 microns (0.200 mm). In other embodiments, the second layer 3200 can be between about 50 microns (0.050 mm) and about 1000 microns (0.100 mm).

In some embodiments, the layers 3100, 3200 forming the multi-chamber packaging described herein can be produced out of a combination of any one or more of the following materials: polyethylene (PE), low density polyethylene (LDPE), composites of LDPE, linear low-density polyethylene (LLDPE), high density poly ethylene (HDPE), polychlorotrifluoroethylene (PCTFE), ethylene tetrafluoroethylene (ETFE), polytetrafluoroethylene (PTFE), fluorinated ethylene propylene (FEP), polyurethane, polyimides (coats or non-coated), polyvinyl chloride (PVC), perfluoroalkoxy alkane (PFA), ethylene-vinyl acetate (EVA), polyvinylidene fluoride or polyvinylidene difluoride (PVDF), THV (a polymer of tetrafluoroethylene, hexafluoropropylene and vinylidene fluoride), PFE (Poly(fluorenylene ethynylene)), nylon, and/or composite of nylon. In some embodiments, any of the multi-chamber packaging using the materials above can be co-extruded and/or laminated. In some embodiments, any of the multi-chamber packaging using the materials above can further include aluminum foil laminate, aluminum oxide laminate, or laminated or co-extruded with aluminum oxide. In some embodiments, any of the multi-chamber packaging can be laminated with a layer of alder or any other suitable adhesive. In some embodiments, the material of the first layer 3100 and the material second layer 3200 are the same. In other embodiments, the material of the first layer 3100 is different from the material of the second layer 3200. For example, the material and/or thickness of the second layer 3200 may be selected such that a rigidity of the second layer 3200 is greater than the rigidity of the first layer 3100.

The materials from which the first layer 3100 and the second layer 3200 are selected to ensure that the two layers can be joined to hermetically seal the storage volume 3060 within which packaging containing the biological material G is stored while also retaining the desired flexibility. The two layers can be joined together at the second end portion 3020 and along the side edges 3030 by any suitable mechanism, such as, for example, by heat bonding or by an adhesive. As shown in FIG. 13, regions near the edge 3111 3112 are configured to be joined together after the containers are loaded into the various storage volumes 3060 to form a closing seal 3113. In this embodiment, the opening 3070 defined by edges on layer 3100. These edges could be formed by a cut or slit in the layer. In some embodiments, the closing seal 3113 is a permanent seal that is openable by destroying the seal and/or the layers 3100, 3200. For example, the closing seal 3113 can include a heat seal between layer 3100 and layer 3200. In other embodiments, the closing seal is a peelable seal that is openable by separating or peeling the sealed layers or edges with a force that is less than what tears the first layer 3100 or the second layer 3200. The peelable seal can be configured to have any suitable failure (or peel) mechanism and can be of any suitable peel strength. By providing a peelable seal, the biologic material G (or any of the stored products retained within the overwrap assembly 3000 can be aseptically presented once peeled apart.

In accordance with various embodiments, each of the storage volumes 3060 can also be subdivided for storage of multiple different items. For example, the product (e.g., container assembly 1000) can be inserted, then a seal line can be applied closing off the volume containing this first product. This can be done by providing enough room for a second product to be inserted through the same opening (e.g., a label to the product). Then a second seal can be applied closing off the second products volume.

In some embodiments, the separable overwrap assembly 3000 includes a volume separating frangible region 3400. The volume separating frangible region 3400 is a region that facilitates the separation of one flexible container (e.g., 3051) from one or more other flexible containers (e.g., 3052) as shown in FIG. 15. The frangible region 3400 can include perforations, thinning of material, stress risers suitable to directional tearing, adhesive attached otherwise detached containers or any other suitable mechanism for separating portions of the overwrap assembly 3000 layers from one another. In some embodiments, the overwrap container 3000 can include one or more transverse perforations 3420 positioned transversely between containers (e.g., between 3051 and 3052 and/or 3052 and 3053) shown in FIGS. 12-14. In some embodiments, the overwrap assembly 3000 can include one or more longitudinal perforations positioned longitudinally between container volumes. As shown in FIG. 15, the frangible regions are separated and a flexible container (e.g., flexible container 3051) is removable from the overwrap assembly 3000 without compromising the structure of the remaining flexible containers (e.g., flexible containers 3052-3053). The separation is shown by arrows D in FIG. 15. The frangible region 3400 can divide the various separable flexible containers 3050, 3051, 3052, 3053 in any suitable way to provide the internal containers as appropriate for the medical process occurring. It will be appreciated that other shapes of the containers, seals, and frangible regions are applicable as well. In some embodiments, provided herein, the two layers (e.g., 3100, 3200) can be provided as tubular material that is flattened forming two longitudinal connections between the layers on the flattened longitudinal edges of the tubular material (e.g., layflat tubular film).

In some embodiments, the separable overwrap assembly 3000 includes a volume opening frangible region 3500 (shown in FIGS. 12-13 as a stippled region). The volume opening frangible region 3500 is a region that facilitates the opening of the separable flexible container 3050, 3051, 3052, 3053 for access into the container volume 3060. In various examples, the connection between the first layer and the second layer can be a peelable connection such that the frangible region includes areas in which the first layer and the second layer can be peeled apart after connection. For example, in some embodiments, the peelable seal 3550 can be an adhesive-based seal in which an adhesive layer pulls back from one of the first layer 3100 or the second layer 3200 when the first layer 3100 is peeled apart from the second layer 3200. In other embodiments, the peelable seal can be a cohesive seal in which an adhesive layer or intermediate layer fails within itself when the first layer 3100 is peeled apart from the second layer 3200. The peelable seal 3550 can be produced by any suitable mechanism as described herein, such as, for example, by a heat-sealing operation. The seal and/or the layers 3100, 3200, whether peelable or permanent hermetically seals the storage volume 3060.

By including the peelable seal 3550, the overwrap assembly 3000 reduces or eliminates the need for a separate tool to cut or tear the separable flexible container 3050, 3051, 3052, 3053 to retrieve the single-chamber container or the multi-chamber container containing tissue and/or biologic materials. Additionally, by including the peelable seal 3550, the overwrap assembly 3000 reduces or eliminates the production of particulate matter or other debris that may result from cutting or tearing the flexible separable container 3050, 3051, 3052, 3053. Moreover, the peelable seal 3550 can facilitate opening the overwrap assembly 3000 in a predetermined fashion and/or in a predetermined direction (e.g., from the first end portion 3010 towards the second end portion 3020). The inclusion of the peelable seal 3550 enables a single separable flexible container 3050, 3051, 3052, 3053 to be opened without disturbing the remaining separable flexible container 3050, 3051, 3052, 3053 to ensure that the unopened separable flexible container 3050, 3051, 3052, 3053 (and the contents within) remain sterile and aseptic.

The peelable seal 3550 can be of any suitable geometry to facilitate the desired peel direction, peel strength, and the like. For example, in some embodiments, the peelable seal 3550 can be an angled seal that provides for peel tabs 3560 that can be grasped by the user to peel the first layer 3100 from the second layer. Similarly stated, in some embodiments, the peelable seal 3550 can be a chevron seal having any suitable angle.

As discussed above in other examples, the frangible region 3400 can be a stress concentration riser. The stress concentration riser can include any suitable feature to initiate tear across the volume. For example, the stress concentration riser can include a tick or perforations at the edges of the volume with sharp points suitable to initiate a tear into the volume 3060.

The embodiment as illustrated in FIGS. 12-15 are operated as an example of an overwrap. The overwrap assembly 3000 can contain smaller containers or containers assemblies (such as the container assemblies described herein) having biological material G. As some material is used, a small section of the layer 3100 can be peeled away exposing just a single container assembly (e.g., container assembly 4000 as shown in FIG. 15.) In some embodiments, the overwrap assembly 3000 can also or alternatively be implemented as the primary flexible container assembly for storing the biological material G directly. The individual separable flexible container 3050, 3051, 3052, 3053 can be sized or shaped to conform to the type of container intended to be stored in the volume 3060. The containers or container assembly could also be shaped to conform to the volume 3060 of the overwrap assembly 3000. Different sizes or shapes of containers or container assemblies could be nested into the volume 3060 of overwrap assembly 3000. Different materials could also be included in the various containers or container assemblies included in the overwrap assembly 3000.

Figure 19:
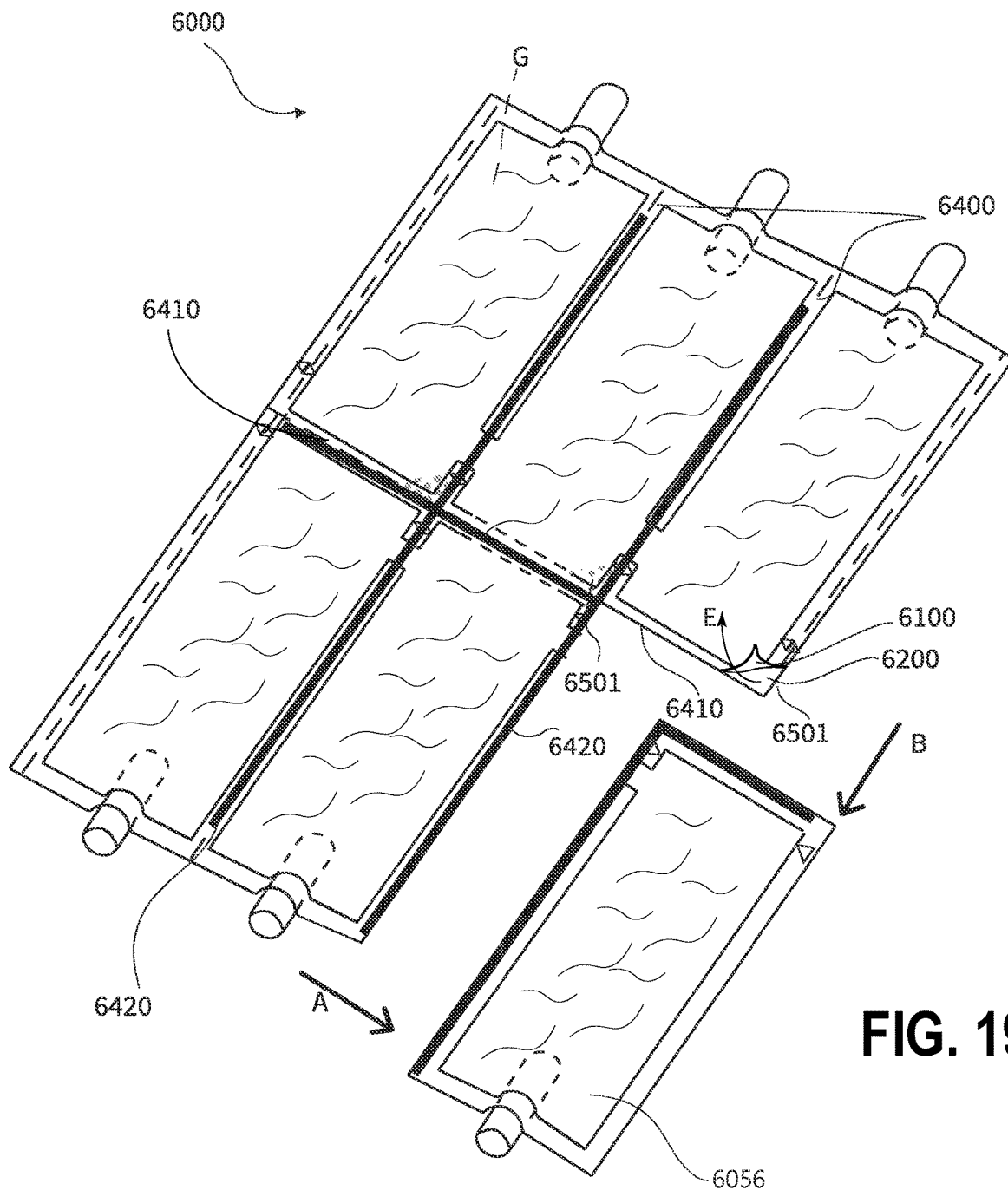
FIG. 19 is a schematic illustration of the multi-chamber container assembly of FIG. 17, in a third configuration.
Figure 20:
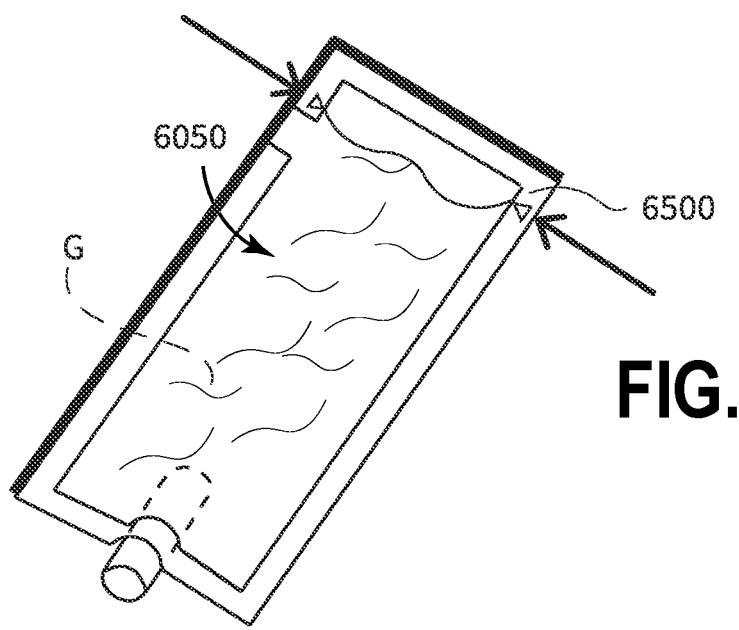
FIG. 20 is a schematic illustration of the multi-chamber container assembly of FIG. 17, in a fourth configuration.
Figure 21:
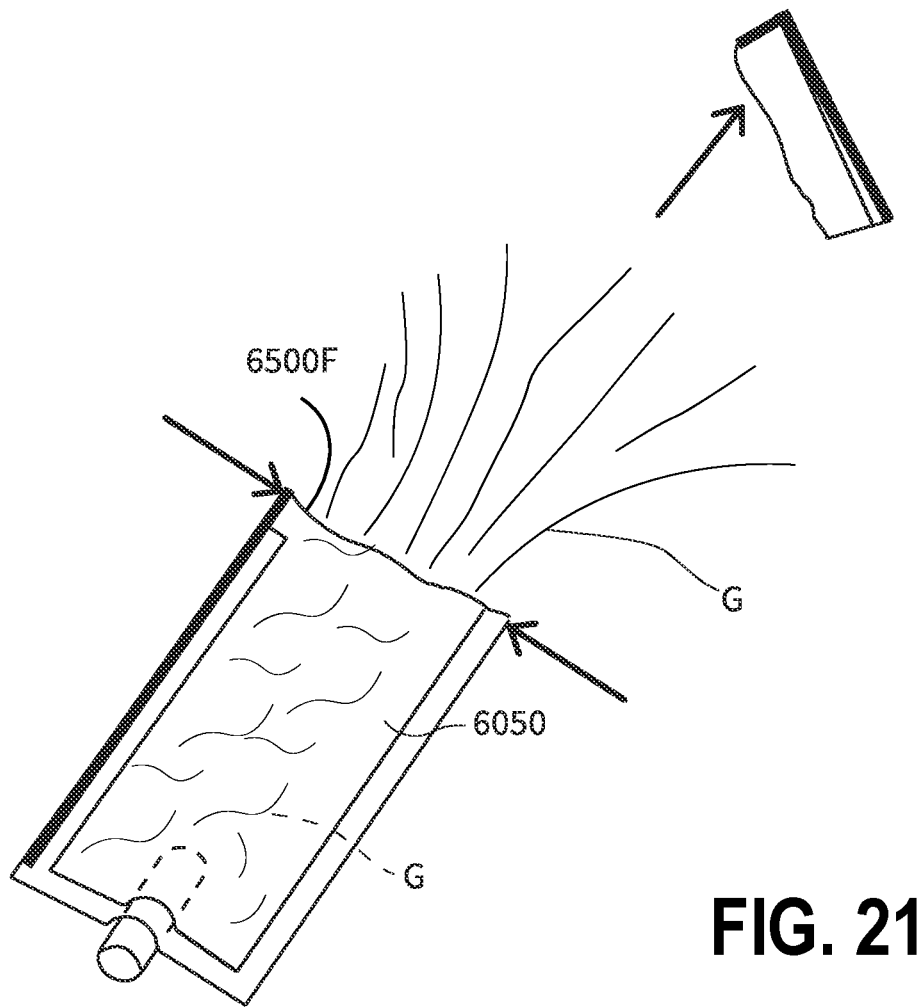
FIG. 21 is a schematic illustration of the multi-chamber container assembly of FIG. 17, in a fifth configuration.

FIGS. 17-21 are schematic illustrations of a multi-chamber container assembly 6000 (also referred to herein as container assembly) according to an embodiment. The container assembly 6000 is shown in a first (unfilled) configuration (FIG. 17), a second (filled and sealed) configuration (FIG. 18), a third (or separating) configuration (FIG. 19), a fourth (or separated) configuration (FIG. 20) and, a fifth (or open) configuration with the contents removed (FIG. 21). The container assembly 6000 (and any of the container assemblies described herein) can be used to store any of the tissue and biological materials described herein, and/or to perform any of the methods described herein. As described herein, the container assembly 6000 provides a container that can be used for storage, transport, processing, and/or rehydration of biologic materials, tissues, or other suitable products. The container assembly 6000 also includes a first layer 6100, a second layer 6200 and one or more seals 6300 connecting the first layer 6100 and the second layer 6200. The one or more seals 6300 form side edges and a center seam of a set of separable, multiple separable flexible containers 6051, 6052, 6053, 6054, 6055, and 6056.

Figure 18:
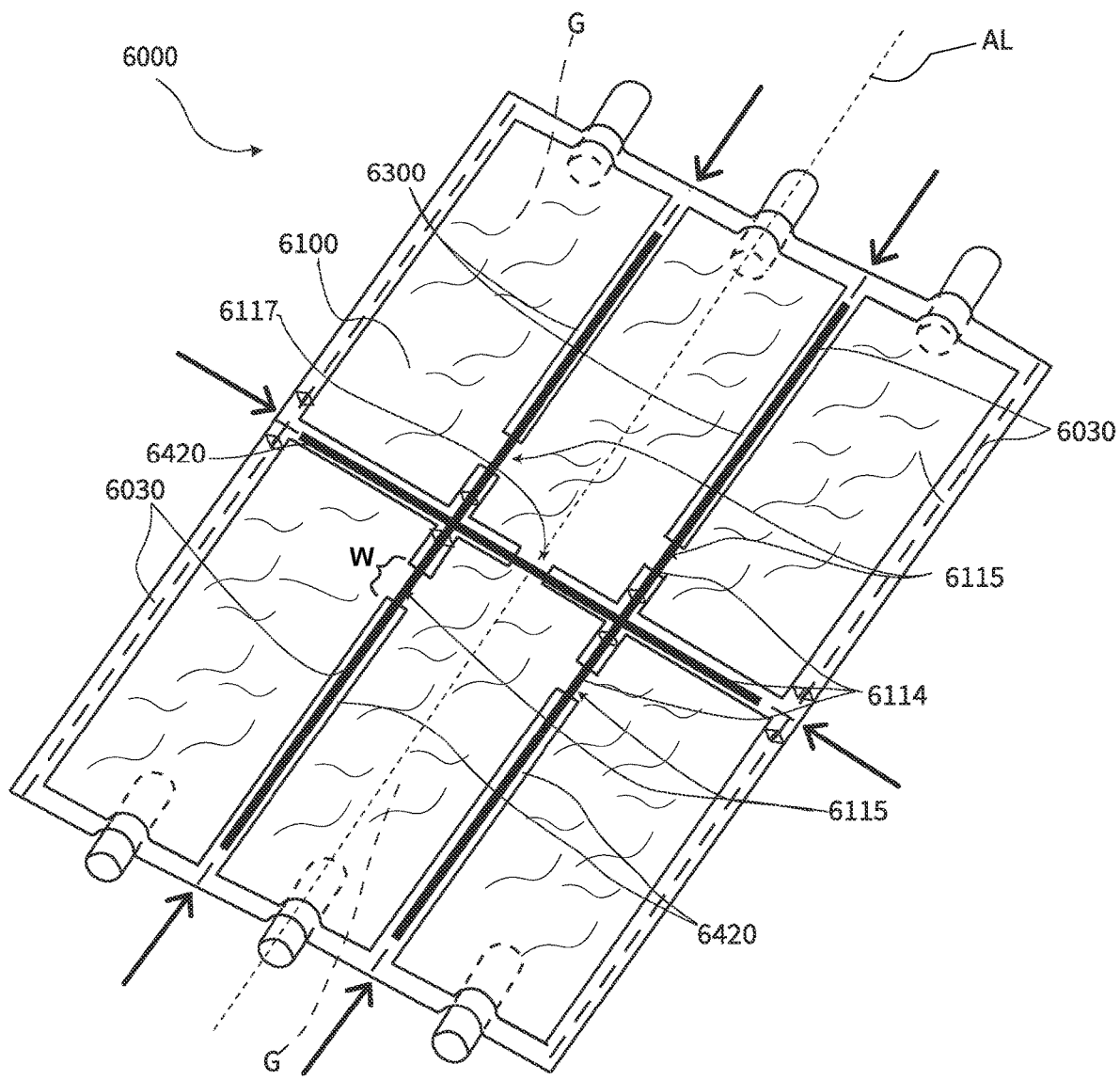
FIG. 18 is a schematic illustration of the multi-chamber container assembly of FIG. 17, in a second configuration.

Each of the multiple separable flexible containers 6051, 6052, 6053, 6054, 6055, 6056 includes a first end portion 6010, a second end portion 6020, and a pair of side edges 6030 that extend from the first end portion 6010 and the second end portion 6020. The separable flexible containers 6051, 6052, 6053, 6054, 6055, 6056 define a longitudinal axis AL that extends longitudinally from the first end portion 6010 and the second end portion 6020 (although only one longitudinal axis AL is shown in FIGS. 17 and 18, each of the separate containers can also define its own longitudinal axis). Each of the separable flexible containers 6051, 6052, 6053, 6054, 6055, 6056 is constructed from the first layer 6100 and the second layer 6200 coupled together to define a storage volume 6070.

In accordance with some embodiments, the assembled separable flexible container 6051, 6052, 6053, 6054, 6055, 6056 includes openings 6115, 6117 defined by the seals 6300 between the separate volumes of each separable flexible container. In some embodiments, adjacent containers positioned laterally of the axis AL can be connected via openings 6115 defined by gaps in the seal 6300. In some embodiments, adjacent containers positioned along the axis AL can be connected via openings 6117 defined by gaps in the seal 6300. As shown, in FIG. 17, the biological material G can suitably flow from one volume to another volume through the openings 6115, 6117. As shown in FIG. 18, the opening 6117 or the opening 6115 can include an opening width W. In some embodiments, the opening width W is less than the length of the seal 6300 that defines the opening and its width W. For example, the width W is less than half the length of the seals 6300 that define the opening. In another example, the width W is less than a quarter of the length of the seals 6300 that define the opening. In another example, the width W is from a tenth of the length of the seals 6300 to a quarter of the length of the seal 6300. In some embodiments, the width of the openings is any suitable width to allow the material G to flow from one container to a connecting container.

In accordance with some embodiments, the openings 6115, 6117 defined by the seals 6300 can be closed after each of the flexible container 6051, 6052, 6053, 6054, 6055, 6056 volumes contain (or have been filled with) the desired material. In one example, as shown in FIG. 18, a heat seal 6114 can be applied across the openings 6115, 6117. Similarly stated, a portion of the first layer 6100 and a portion of the second layer 6200 can be heat sealed to close one or more of the openings 6115, 6117. In other examples, other suitable seal types can be alternatively applied across the openings 6115, 6117. For example, an adhesive seal can be applied. In some embodiments, seals can extend across a potion of the width of the container assembly 6000. In some embodiments, seals can extend across the entire width of the container assembly 6000. In some embodiments, seals can extend across a portion of the length of the container assembly 6000. In some embodiments, seals can extend across the entire length of the container assembly 6000. In some embodiments, seals can extend across the opening 6115, 6117 and into the seal 6300 a limited amount such that they are limited to only sufficiently closing the opening to isolate each volume. By closing the openings 6115, 6117, each volume of the flexible container can be isolated allowing for separation shown in FIGS. 19-21 discussed in more detail below.

In some embodiments, as illustrated in FIGS. 17-21, each of the multiple separable flexible containers 6051, 6052, 6053, 6054, 6055, 6056 includes a at least one opening 6080. In some embodiments, the opening 6080 is a port. For example, as shown in FIGS. 17-21, the two layers 6100, 6200 respectively are joined at the second end portion 6020 with the port 6080 therebetween, and the two side edges 6030 are joined together. The port 6080 is coupled to the second end portion 6020 of the container assembly 6000 and is configured to allow fluid communication between a volume outside of the container assembly 6000 and the storage volume 6070. Thus, the port 6080 can be used to provide access to the storage volume 6070 and the biological material G after any additional opening(s) have been sealed closed (see e.g., embodiments in FIGS. 6-10). The port 6080 can also be coupled to a vacuum source to evacuate the storage volume for storage of the biological material G.

The port 6080 can be any suitable port that selectively provides fluid communication to the storage volume 6070. For example, the port 6080 can include a tube, a valve, and/or a cap. In some embodiments, the port 6080 can be a needle-free port. In some embodiments, the port 6080 can be a swabable connector. Similarly stated in some embodiments, the port 6080 can have external surfaces and can be devoid of recesses or crevices such that the port 6080 can be easily wiped or "swabbed" to maintain sterility during use. In some embodiments, the port 6080 can include any of the barbed, swabable valves produced by the Halkey-Roberts Corporation, such as the 6455 series of swabable valves. In other embodiments, the port 6080 (and any of the ports described herein) need not be either a swabable connector or a needle-free port; any suitable port can be employed. In some embodiments, the port 6080 can include a male or female luer fitting.

Although the port 6080 is shown as being coupled at the second end portion 6020 of the separable flexible container 6051, 6052, 6053, 6054, 6055, 6056, in other embodiments, the port 6080 (and any of the ports described herein) can be coupled at any location and to any portion of the separable flexible container 6051, 6052, 6053, 6054, 6055, 6056. For example, in some embodiments, the port 6080 (and any of the ports described herein) need not be coupled to an end of the container that is opposite from the end of the container that includes the peelable seal. The port 6080 (and any of the ports described herein) can be offset from a center line of the separable flexible container 6051, 6052, 6053, 6054, 6055, 6056. For example, in some embodiments, the port can be located at a corner of the separable flexible container, 6051, 6052, 6053, 6054, 6055, 6056. Moreover, the in some embodiments, the port 6080 (and any of the ports described herein) can be coupled in a central portion of the separable flexible container 6051, 6052, 6053, 6054, 6055, 6056.

FIGS. 17-21 show a single ported opening on each of the separable flexible containers 6051, 6052, 6053, 6054, 6055, 6056. In some embodiments, some containers of the container assembly 6000 will have multiple openings and some will not. For example, FIGS. 6-10 illustrate a set of openings 2070 (which include the openings 2071, 2072, 2073, 2074, 2075, 2075, 2076). The embodiment, in FIGS. 17-21 could include similar openings opposite the ported opening. Such an opening could allow for the placement of supported tissue within the container. After closing these openings the various fluids used to treat the tissue could flow through the openings 6115 and 6117 from a single container to each of the connected containers. However, for clarity, the containers of FIGS. 17-21 are not shown with a second opening. Instead, the openings between volumes are shown for clarity.

In other embodiments, additional container combinations, shapes, sizes, and contents can be included in the container assembly 6000. For example, although the container assembly 6000 is shown with rectangularly-shaped separable flexible containers, any of the container assemblies described herein can include separable flexible containers with perimeters of other shapes, including but not limited to, square, triangle, trapezoid, or funnel shapes. In some embodiments, the seal 6300 of the container assembly 6000 (or seals of any of the container assemblies described herein) can formed as a linear and/or curvilinear form such that an internal volume of a corresponding separable flexible container 6051, 6052, 6053, 6054, 6055, 6056 includes a circular or curved boundary.

The first and second layers 6100, 6200 respectively can be constructed of any suitable material. The first layer 6100 can have a first stiffness and the second layer 6200 can have a second stiffness. In some embodiments, the stiffnesses are the same. In some embodiments the stiffnesses are different. In some embodiments the second stiffness is greater than the first stiffness. In some embodiments, the first stiffness is greater than the second stiffness. In some embodiments, the layers 6100, 6200 respectively can constructed from the same material. In other embodiments, the layers 6100, 6200 respectively can be constructed from a different material and the second stiffness can be different than the first stiffness. In some embodiments, the first layer 6100 can be a thin, peelable film. The first layer 6100 can have any suitable thickness to provide the desired strength, flexibility, and sealing characteristics. For example, in some embodiments, the first layer 6100 can be between about 10 microns (0.010 mm) and about 6000 microns (2.0 mm). In some embodiments, the first layer 6100 can be between about 50 microns (0.050 mm) and about 600 microns (0.200 mm). In other embodiments, the first layer can be between about 50 microns (0.050 mm) and about 1000 microns (0.100 mm). The second layer 6200 can have any suitable thickness to provide the desired strength, flexibility, and sealing characteristics. For example, in some embodiments, the second layer 6200 can be between about 10 microns (0.010 mm) and about 6000 microns (2.0 mm). In some embodiments, the second layer 6200 can be between about 50 microns (0.050 mm) and about 600 microns (0.200 mm). In other embodiments, the second layer 6200 can be between about 50 microns (0.050 mm) and about 1000 microns (0.100 mm).

In some embodiments, the layers 6100, 6200 of the container assembly 6000 (or the material of any of the container assemblies described herein) can be produced out of any one or more of the following materials: polyethylene (PE), low density polyethylene (LDPE), composites of LDPE, linear low-density polyethylene (LLDPE), high density poly ethylene (HDPE), polychlorotrifluoroethylene (PCTFE), ethylene tetrafluoroethylene (ETFE), polytetrafluoroethylene (PTFE), fluorinated ethylene propylene (FEP), polyurethane, polyimides (coats or non-coated), polyvinyl chloride (PVC), perfluoroalkoxy alkane (PFA), ethylene-vinyl acetate (EVA), polyvinylidene fluoride or polyvinylidene difluoride (PVDF), THV (a polymer of tetrafluoroethylene, hexafluoropropylene and vinylidene fluoride), PFE (Poly(fluorenylene ethynylene)), nylon, and/or composite of nylon. In some embodiments, any of the multi-chamber packaging using the materials above can be co-extruded and/or laminated. In some embodiments, any of the multi-chamber packaging using the materials above can further include aluminum foil laminate, aluminum oxide laminate, or laminated or co-extruded with aluminum oxide. In some embodiments, any of the multi-chamber container assemblies can be laminated with a layer of alder or any other suitable adhesive. In some embodiments, the material of the first layer 6100 and the material second layer 6200 are the same. In other embodiments, the material of the first layer 6100 is different from the material of the second layer 6200. For example, the material and/or thickness of the second layer 6200 may be selected such that a rigidity of the second layer 6200 is greater than the rigidity of the first layer 6100.

The materials from which the first layer 6100 and the second layer 6200 are selected to ensure that the two layers 6100, 6200 can be joined to hermetically seal the storage volume 6060 within which the biological material G (or any other stored product described herein) is stored while also retaining the desired flexibility. The two layers 6100, 6200 can be joined together at the second end portion 6020 and along the side edges 6030 by any suitable mechanism, such as, for example, by heat bonding or by an adhesive. This can include applying the seals 6114 to close openings 6115 or 6117.

In some embodiments, the multi-chamber container 6000 includes a volume separating frangible region 6400. The volume separating frangible region 6400 is a region that facilitates the separation of one separable flexible container (e.g., 6056) from one or more other separable flexible containers (e.g., 6055 and/or 6053) as shown in FIG. 19. The frangible region 6400 can include perforations, thinning of material, stress risers suitable to directional tearing, adhesive attached otherwise detached containers or any other suitable mechanism for separating portions of the container assembly 6000 layers from one another. In some embodiments, the container assembly 6000 can include one or more longitudinal perforations 6410 positioned longitudinally between container volumes (e.g., between 6051, 6052, 6053 and 6054, 6055, 6056) shown in FIGS. 17-19. In some embodiments, the container assembly 6000 can include one or more transverse perforations 6420 positioned transversely between containers (e.g., between 6051, 6054 and 6052, 6055 and/or 6052, 6055 and 6053, 6056) shown in FIGS. 17-19. As shown in FIG. 19, the frangible regions are separated and a flexible container (e.g., flexible container 6056) is removable from the flexible container assembly 6000 without compromising the structure of the remaining flexible containers (e.g., flexible containers 6051-2055). The separation is shown by arrows A and B in FIG. 19. While the embodiment shown in FIGS. 17-19 show rectangular containers 6051-6056 separated by an H shaped seal and frangible region 6400 positioned therebetween. However, it will be appreciated that other shapes of the containers, seals, and frangible regions are applicable as well. For example, FIG. 12 illustrates a container assembly 4000 with trapezoidal shaped separable containers. In some embodiments, flat layers can be provided with minimal attachment and custom separable containers can be formed thereon. In some embodiments, provided herein, the two layers (e.g., 6100, 6200) can be provided as tubular material that is flattened forming two longitudinal connections between the layers on the flattened longitudinal edges of the tubular material (e.g., layflat tubular film). In some embodiments, the frangible region 6400 can be applied after seals 6114. In other embodiment, the seals 6114 can be applied over or along the side of the frangible region 6400.

In some embodiments, the separable flexible container assembly 6000 includes a volume opening frangible region 6500 (see FIG. 20). The volume opening frangible region 6500 is a region that facilitates the opening of each of the separable flexible containers 6051, 6052, 6053, 6054, 6055, 6056 into their respective container volumes 6070. In various examples, as discussed above, the connection between the first layer 6100 and the second layer 6200 can be a peelable connection such that the frangible region includes areas in which the first layer and the second layer can be peeled apart after connection. For example, FIG. 19 illustrates a frangible region 6500 including a peelable separation region 6501. The peelable separation region 6501 allows for the separation of the first layer 6100 and the second layer 6220. The initiation of this peel allows for the two layers to be at least partially separated and in some embodiments entirely separated. Other examples of peelable connections are discussed in more detail above with reference to the embodiments shown in FIGS. 12-15. The examples of peelable separation regions shown in FIGS. 12-15 are applicable to the embodiments shown in FIGS. 17-21. In other examples, the frangible region 6500 can be a stress concentration riser as illustrated in FIGS. 17-21. The stress concentration riser can include any suitable feature to initiate tear across the volume. As illustrated in the embodiments of FIGS. 17-21, this can include tick perforations at the edges of the volume 6060 with sharp points suitable to initiate a tear 6500F into the volume 6060. In some embodiments, the tick perforations forming the frangible region 6500 is a V-shaped perforation. In some embodiments, as shown in FIG. 19, two frangible regions 6500 are formed adjacent to each other during the formation of the seal 6300 or after the formation of the seal 6300. A first frangible region of the adjacent frangible regions is operable to open a first one of the separable flexible containers (e.g., separable flexible container 6056) and a second frangible region is operable to open a second one of the separable flexible containers (e.g., separable flexible container 6055).

The container assemblies disclosed herein (e.g., container assemblies 1000, 2000, 3000, 4000, 5000, 6000) could be any longitudinal length having any number of contains distributed longitudinally. Additionally, or alternatively, the container assemblies (e.g., 1000, 2000, 3000, 4000, 5000, 6000) could be any transverse width having any number of contains distributed transversely. Additionally, or alternatively, the container assemblies (e.g., 1000, 2000, 3000, 4000, 5000, 6000) could be any stack height having additional layers forming a stack of volumes distributed along the height of the container assembly.

In accordance with various embodiments, each of the containers or container assemblies discussed herein can also include holes through the sealed region. The holes can enable the separated individual containers to be hung on a medical stand such as an IV pole. Thus, the container assemblies can be subdivided and readily usable in a medical environment to dispense the contents thereof.

While the discussion herein has be directed to the storage of biological material, it is appreciated that other materials could be stored in the various packaging as well. For example, any of the containers or container assemblies described can store pharmaceutical ingredients (including active pharmaceutical ingredients, dilutents, preservatives, inert components, or other pharmaceutical ingredients). Such pharmaceutical ingredients can be packaged and stored in any of the containers or container assemblies described herein for storage, distribution, and later compounding, mixing, or other pre-delivery preparation steps.

As another example, medical instruments, labels, directions, etc. could be stored in any of the containers or container assemblies described herein. The various disclosures herein could also apply to other industries as well. For example, the container assemblies disclosed herein could package food products, toys, tools, clothing apparel, agricultural products, etc.

In accordance with various embodiments, each of the containers within the various container assemblies can include passages that extend between the various container volumes. In this way, liquid, paste, gelatinous or similar materials could flow between one or more of the connected volumes as a single volume is filled. Once filled, one or more seals could be used to seal each of the volumes.

While some embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

Although some embodiments have been described as having particular features and/or combinations of components, other embodiments are possible having a combination of any features and/or components from any of embodiments as discussed above. Aspects have been described in the general context of medical devices, and more specifically tissue packaging devices, but inventive aspects are not necessarily limited to use in medical devices and tissue packaging.

What is claimed is:

1. An apparatus, comprising:
 a separable flexible container including a first layer coupled to a separate second layer via a plurality of seals to define at least a first storage volume and a second storage volume, the first storage volume being configured to contain a first stored product, the second storage volume being configured to contain a second stored product, the first stored product and the second stored product being for use in one or more medical procedures, a first portion of the first layer or the second layer defining a first opening into the first storage volume and a second portion of the first layer or the second layer defining a second opening into the second storage volume;
 a first port coupled to the first storage volume, the first layer being joined to the second layer with the first port therebetween;
 a second port coupled to the second storage volume, the first layer being joined to the second layer with the second port therebetween;
 a fold line positioned between the first storage volume and the second storage volume, the first layer and the second layer configured to be folded along the fold line to move a position of the first opening relative to the second opening to facilitate a loading of the first stored product via the first opening and the second stored product via the second opening; and
 a frangible region positioned along at least one seal of the plurality of seals and configured for separation of the first storage volume from the second storage volume.

2. The apparatus of claim 1, wherein the first layer and the second layer are configured to be permanently sealed together thereby closing the first opening and the second opening to establish a hermetic sealing of the first storage volume and the second storage volume following the loading of the first stored product and the second stored product.

3. The apparatus of claim 1, wherein:
 the first port is on an opposite edge of the first storage volume relative to the first opening; and
 the second port is on an opposite edge of the second storage volume relative to the second opening.

4. The apparatus of claim 1, wherein:
 the first opening is defined by a first slit in one of the first layer or the second layer;
 the second opening is defined by a second slit in one of the first layer or the second layer; and
 the second opening is substantially parallel to the first opening.

5. The apparatus of claim 1, wherein the first port and the second port are aligned along a longitudinal axis defined by the first storage volume and the second storage volume.

6. The apparatus of claim 5, wherein:
 the first opening and the second opening are positioned along the longitudinal axis;
 the first opening extends laterally from the longitudinal axis; and
 the second opening extends laterally from the longitudinal axis.

7. The apparatus of claim 1, wherein:
 the separable flexible container includes a first destructive opening region that facilitates access to the first stored product for use in one or more medical procedures without affecting a hermetic sealing of the second storage volume; and
 the separable flexible container includes a second destructive opening region that facilitates access to the second stored product for use in one or more medical procedures without affecting the hermetic sealing of the second storage volume.

8. The apparatus of claim 7, wherein:
 each of the first destructive opening region and the second destructive opening region includes a stress concentration riser positioned to initiate a tear to access the respective storage volume; and
 each stress concentration riser is surrounded by a seal of the plurality of seals of the separable flexible container.

9. The apparatus of claim 7, wherein:
the first destructive opening region is a destructive peelable seal that is openable by separating the first layer from the second layer with a force that is less than a force required to tear either of the first layer or the second layer; and
the destructive peelable seal is configured as a single-use seal.

10. The apparatus of claim 1, further comprising a support structure, the support structure being configured to support the first stored product, a stiffness of the support structure is greater than each of a stiffness of the first layer and a stiffness of the second layer.

11. The apparatus of claim 10, wherein the first opening is sized to receive the support structure.

12. The apparatus of claim 1, wherein:
the first opening extends along a portion of a length of an end of the first storage volume adjacent to the fold line, and the portion is less than the length of the end; and
the second opening extends along a portion of a length of an end of the second storage volume adjacent to the fold line opposite the first opening, and the portion is less than the length of the end.

13. An apparatus, comprising:
a separable flexible container including a first layer coupled to a separate second layer via a plurality of seals to define at least a first storage volume and a second storage volume, a first portion of the first layer or the second layer defining a first opening into the first storage volume and a second portion of the first layer or the second layer defining a second opening into the second storage volume;
a frangible fold line positioned between the first storage volume and the second storage volume, the frangible fold line affecting a position of the first opening relative to the second opening while maintaining a flexible coupling between the first storage volume and the second storage volume, the frangible fold line facilitating the separation of either the first storage volume or the second storage volume from the separable flexible container;
a first port coupled to the first storage volume within a first seal of the plurality of seals, the first opening being positioned between the frangible fold line and the first port; and
a second port coupled to the second storage volume within a second seal of the plurality of seals, the second opening being positioned between the frangible fold line and the second port, the first port configured to allow fluid communication between the first storage volume and an external volume, the second port configured to allow fluid communication between the second storage volume and the external volume.

14. The apparatus of claim 13, wherein:
the first opening extends along a portion of a total length of an end of the first storage volume adjacent to the frangible fold line; and
the second opening extends along a portion of a total length of an end of the second storage volume adjacent to the frangible fold line opposite the first opening.

15. The apparatus of claim 13, wherein the first layer and the second layer are configured to be sealed together to close the first opening and the second opening to establish a hermetic seal of each of the first storage volume and the second storage volume after a stored product is loaded into each of the first storage volume and the second storage volume.

16. The apparatus of claim 15, wherein:
the separable flexible container includes a first destructive opening region that facilitates access to the first storage volume without affecting the hermetic seal of the second storage volume;
the separable flexible container includes a second destructive opening region that facilitates access to the second storage volume without affecting the hermetic seal of the first storage volume; and
the first destructive opening region and the second destructive opening region are peelable seals.

17. The apparatus of claim 13, wherein:
the plurality of seals further defines a third storage volume, a longitudinal edge of the third storage volume is removably coupled to a longitudinal edge of the first storage volume by a first frangible region;
the plurality of seals further defines a fourth storage volume, a longitudinal edge of the fourth storage volume is removably coupled to a longitudinal edge of the second storage volume by a second frangible region; and
the third storage volume is separated from the fourth storage volume by the frangible fold line.

18. The apparatus of claim 17, wherein:
the first frangible region is perpendicular to the frangible fold line; and
the second frangible region is perpendicular to the frangible fold line.

19. The apparatus of claim 17, wherein:
the plurality of seals further defines a perforation positioned between the longitudinal edge of the third storage volume and the longitudinal edge of the first storage volume, the perforation facilitating the opening of at least one of the first storage volume or the third storage volume, the perforation being surrounded by the first layer and the second layer.

20. The apparatus of claim 1, wherein a thickness of the first layer is different than a thickness of the second layer.

21. The apparatus of claim 1, wherein:
the first storage volume and the second storage volume are two of a plurality of storage volumes defined by the first layer and the second layer;
the plurality of storage volumes includes more than two storage volumes; and
each of the storage volumes of the plurality of storage volumes is filled prior to separation from any other storage volume of the plurality of storage volumes.

22. A container assembly, comprising:
a first layer extending along a maximal length and a maximal width of the container assembly;
a separate second layer extending along the maximal length and the maximal width of the container assembly, the second layer being coupled to the first layer via a plurality of seals to define a first plurality of separable storage volumes and a second plurality of separable storage volumes, each storage volume of the first plurality of separable storage volumes and the second plurality of separable storage volumes being configured to contain a stored product, the first layer or the second layer defining a first plurality of openings, each of the first plurality of openings providing access into a storage volume of the first plurality of separable storage volumes, the first layer or the second layer defining a second plurality of openings, each of the second plurality of openings providing access into a storage volume of the second plurality of separable storage volumes; and a center seam separating the first plurality of separable storage volumes from the second plurality of separable storage volumes, the first layer and the second layer configured to be folded along the center seam to move a position of the first plurality of openings relative to the second plurality of openings to facilitate a loading of the first plurality of separable storage volumes and the second plurality of storage volumes, wherein:

each storage volume of the first plurality of separable storage volumes is separated from an adjacent storage volume of the first plurality of separable storage volumes via a seal of the plurality of seals, the seal defines a frangible region and a stress concentration riser, the stress concentration riser is surrounded by the seal, the frangible region is configured to facilitate the separation of each storage volume from the adjacent storage volume.

\* \* \* \* \*

UNITED STATES PATENT AND TRADEMARK OFFICE
CERTIFICATE OF CORRECTION

| | |
|---|---|
| PATENT NO. | : 11,890,819 B2 |
| APPLICATION NO. | : 17/703042 |
| DATED | : February 6, 2024 |
| INVENTOR(S) | : Tara C. Ramsey |

It is certified that error appears in the above-identified patent and that said Letters Patent is hereby corrected as shown below:

In the Claims

Column 31, Line 8 (Claim 22): the phrase "plurality of storage volumes" should be -- plurality of separable storage volumes --

Signed and Sealed this
Twenty-sixth Day of March, 2024

Katherine Kelly Vidal
*Director of the United States Patent and Trademark Office*